(12) United States Patent
Chen

(10) Patent No.: US 12,629,284 B2
(45) Date of Patent: *May 19, 2026

(54) EAR CLEANING ARRANGEMENT

(71) Applicant: Qinbin Chen, Shantou City (CN)

(72) Inventor: Qinbin Chen, Shantou City (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/747,435

(22) Filed: Jun. 18, 2024

(65) Prior Publication Data

US 2025/0302671 A1     Oct. 2, 2025

Related U.S. Application Data

(63) Continuation of application No. 18/617,600, filed on Mar. 26, 2024.

(51) Int. Cl.
| | |
|---|---|
| *A61F 11/00* | (2022.01) |
| *A61B 1/00* | (2006.01) |
| *A61B 1/05* | (2006.01) |
| *A61B 1/06* | (2006.01) |
| *A61B 1/07* | (2006.01) |
| *A61B 1/12* | (2006.01) |

(Continued)

(52) U.S. Cl.
CPC ........ *A61F 11/006* (2013.01); *A61B 1/00066* (2013.01); *A61B 1/00087* (2013.01); *A61B 1/00101* (2013.01); *A61B 1/05* (2013.01); *A61B 1/0676* (2013.01); *A61B 1/07* (2013.01); *A61B 1/128* (2013.01); *A61B 1/227* (2013.01); *G02B 6/0008* (2013.01); *A61F 2240/004* (2013.01)

(58) Field of Classification Search
CPC ..... A61B 1/227; A61B 1/051; A61B 1/00096; A61B 1/00101; A61F 11/006
See application file for complete search history.

(56) References Cited

U.S. PATENT DOCUMENTS

| | | | | |
|---|---|---|---|---|
| 2004/0249244 A1* | 12/2004 | Koda | .................... | A61F 11/006 |
| | | | | 600/200 |
| 2019/0307322 A1* | 10/2019 | Wujciak | ............ | A61B 1/00101 |
| 2020/0093644 A1* | 3/2020 | Kraitzer | ................ | A61F 11/006 |

(Continued)

FOREIGN PATENT DOCUMENTS

| | | | | | |
|---|---|---|---|---|---|
| CN | 112294534 A | * | 2/2021 | ............ | A61F 11/006 |

OTHER PUBLICATIONS

Bebird® R3 Ear Wax Removal Cleaner,0.15inch 1080P HD Ear Camera Lens with 6 LED Lights Intelligent Otoscope for iPhone, Android Phone(White) Amazon, 2021 (retrieved on Jun. 5, 2024) <URL: https://www.amazon.com/BEBIRD%C2%AE-Removal-0-15inch-Intelligent-Otoscope/dp/B097GN36GC> (Year: 2021).*

(Continued)

*Primary Examiner* — Alexandra L Newton

(74) *Attorney, Agent, or Firm* — Che-Yang Chen

(57) ABSTRACT

A an ear cleaning arrangement includes a fixing assembly comprising a fixing rod and a handle, wherein the fixing rod is connected to the handle, an ear spoon assembly which is arranged to be connected to the fixing rod for cleaning earwax, a camera, and a light source, wherein the camera and the light source are assembled in the fixing rod behind a light guide barrel, so that the ear cleaning arrangement is equipped with a suitable camera for real-time acquisition of images in the ear, so as to facilitate the user in accurately locating and cleaning earwax.

10 Claims, 15 Drawing Sheets

(51) Int. Cl.
    *A61B 1/227*         (2006.01)
    *F21V 8/00*         (2006.01)

(56)            References Cited

U.S. PATENT DOCUMENTS

| | | | |
|---|---|---|---|
| 2020/0315444 A1* | 10/2020 | Ramanujam ........... | A61B 1/307 |
| 2022/0210298 A1* | 6/2022 | Yan ........................ | G03B 17/55 |
| 2023/0277049 A1* | 9/2023 | von Wendorff ...... | A61B 1/0676 |
| | | | 600/109 |

OTHER PUBLICATIONS

English translation of CN 11294534 (Year: 2021).*
Bebird R1 Wax Removal Tool for Ear—Spade Ear Canal Cleaner with Camera 1080P Earscope, Amazon, 2020 (retrieved on Dec. 16, 2024) <URL :https://www.amazon.com/BEBIRD%C2%AE-Removal-Otoscope-Silicone-Compatible/dp/B08M9G18H3/>.*

\* cited by examiner

A

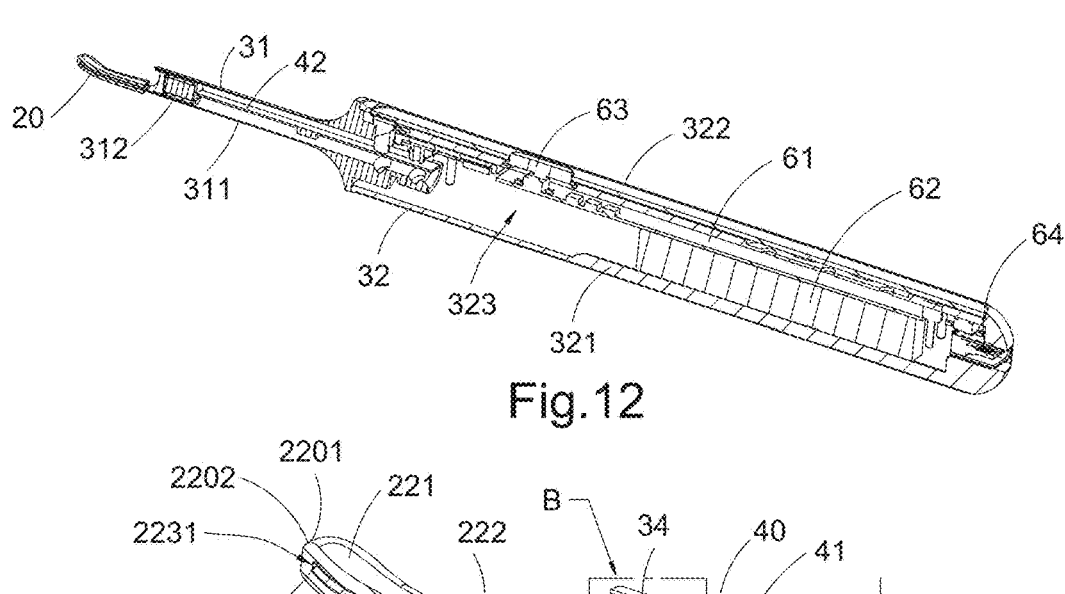
Fig.12
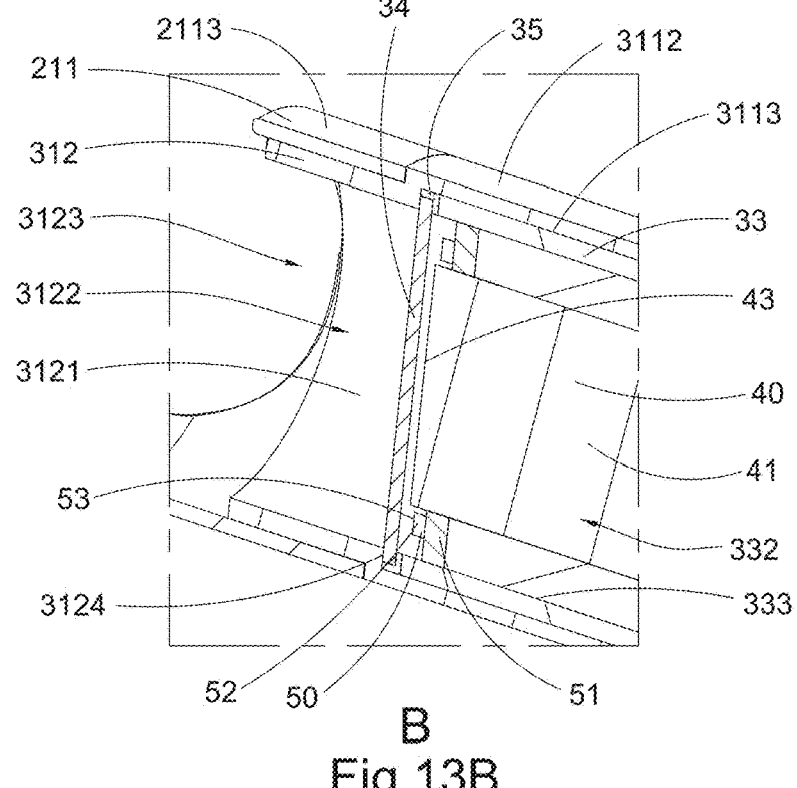
Fig.13A
B
Fig.13B

C

EAR CLEANING ARRANGEMENT

CROSS REFERENCE OF RELATED APPLICATION

This is a Continuation Application that claims the benefit of priority under 35U.S.C. § 120 to a non-provisional application, application Ser. No. 18/617,600, filing date 03/26/2024, wherein the entire content of which is expressly incorporated herein by reference.

BACKGROUND OF THE PRESENT INVENTION

Field of Invention

The present invention relates to an ear cleaning arrangement, and more particularly to an ear cleaning arrangement equipped with a camera to facilitate a user to clean earwax more accurately.

Description of Related Arts

Earwax is a substance secreted in the human ear canal. If there is excessive secretion of earwax or it cannot be discharged normally, it will accumulate in the ear canal, making the ear unclean and unhygienic. In severe cases, it may also cause symptoms such as hearing loss, tinnitus, and ear pain.

When using an ear spoon or a cotton swab to clean earwax, it is difficult to know the position of the earwax in the ear, so it is not easy to completely clean the earwax in the ear. Moreover, if the ear spoon or cotton swab is used improperly, it may result in hurt to the ear canal or eardrum. There is a risk of causing ear canal infection when using ear drops to clean earwax. And the cost is relatively high when turning to a professional for help.

An ear cleaning arrangement with a built-in camera has appeared on the market. This device allows the user to obtain real-time images of their ears to assist and guide the device in cleaning earwax. However, although the visual ear cleaning arrangement allows the user to have a view of the condition in the ear canal, if the camera configuration does not match or the lighting is insufficient, the images may not be clear enough. Inaccurate judgment of the position of the end of the ear cleaning arrangement used to clean earwax may also cause the device to scratch the ear canal and cause infection. Additionally, the camera device generates a large amount of heat during operation. When this heat is transferred to the part of the visual ear cleaning arrangement that comes into contact with the user's ear, it may cause a burning sensation and discomfort.

In addition, the ear cleaning arrangement needs to be cleaned with water before or after use. If the device has poor waterproof performance, it is prone to damage. When there are water droplets remaining on the camera device, it will cause the user to wait for the water on the camera device to evaporate before use, thus wasting the user's time.

SUMMARY OF THE PRESENT INVENTION

This invention is advantageous in that it provides an ear cleaning arrangement which is equipped with a suitable camera for real-time acquisition of images in the ear, so as to facilitate the user in accurately locating and cleaning earwax.

Another advantage of the present invention is to provide an ear cleaning arrangement, wherein a light source is arranged around the camera, and a light source is arranged at the front end of the camera, so that the light emitted from the light source can be evenly guided into the ear and the end of the ear spoon assembly, and prevent external stray light from entering the field of view of the camera, thereby reducing glare or dark spots and providing the user with a clearer image.

Another advantage of the present invention is to provide an ear cleaning arrangement, wherein the light emitting surface of the light source is coplanar with or located behind the lens end surface of the camera, so that the light from the light source can effectively be emitted towards the exit of the light guide barrel to illuminate the ear canal and the ear spoon assembly, thereby avoiding direct exposure of the camera and also avoiding stray light from being directed towards the camera. Moreover, when the waterproof glue is applied to the light source, it also avoids the glue being applied to the lens end surface and affecting the optical imaging effect.

Another advantage of the present invention is to provide an ear cleaning arrangement, wherein the light guide barrel is used to detachably install the ear spoon assembly, and the camera does not extend into the light guide barrel, thereby avoiding the camera from being damaged by compression during the installation of the installation part of the ear spoon assembly into the light guide barrel.

Another advantage of the present invention is to provide an ear cleaning arrangement, wherein after installation of the installation part of the ear spoon and the light guide barrel, the inner wall of the connection structure between the installation part of the ear spoon assembly and the light guide barrel does not form a light channel, thereby avoiding stray light entering the connection structure and forming stray light incident on the camera.

Another advantage of the present invention is to provide an ear cleaning arrangement, wherein the ear spoon assembly can have a different material from the fixing rod, and can be constructed to prevent heat from the fixing rod from being transferred to the end of the ear spoon assembly when the camera is in operation, in order to prevent burning the user's ear.

Another advantage of the present invention is to provide an ear cleaning arrangement, wherein the ear spoon assembly can be constructed of transparent material, thereby avoiding blocking the light emitted by the light source.

Another advantage of the present invention is to provide an ear cleaning arrangement, wherein the ear spoon assembly comprises a rigid inner spoon and a flexible outer spoon, wherein the flexible outer spoon can be detachably fitted an the outer side of the rigid inner spoon, and the end of the flexible outer spoon is coaxial with the center axis of the camera and is used to contact the ear and clean the earwax. Therefore, the user can accurately judge the position of the end of the flexible outer spoon in the image and facilitate the user to operate the ear cleaning arrangement to clean the earwax accurately, and avoid scratching the ear canal and causing infection by the ear spoon assembly.

Another advantage of the present invention is to provide an ear cleaning arrangement, wherein the end of the ear spoon assembly, the center of the camera, and the centers of the two light emitting elements around the camera are coplanar, so as to ensure that the center of the end of the ear spoon assembly and the earwax in the ear can be located in the center of the field of view of the camera, thereby facilitating the user to operate the ear spoon assembly to aim at the earwax for cleaning.

Another advantage of the present invention is to provide an ear cleaning arrangement, wherein a waterproof structure is provided at the assembly position of the camera, so that when the ear cleaning arrangement is cleaned with water, water will not enter the interior of the ear cleaning arrangement and cause damage to the components.

Another advantage of the present invention is to provide an ear cleaning arrangement, wherein a hydrophobic structure is arranged in front of the camera, so that after the ear cleaning arrangement is cleaned with water, water droplets are not easily residue in front of the camera, so that the ear cleaning arrangement can be used in a timely manner without wasting the user's time.

Additional advantages and features of the invention will become apparent from the description which follows, and may be realized by means of the instrumentalities and combinations particularly pointing out in the appended claims.

According to the present invention, the foregoing and other objects and advantages are attained by an ear cleaning arrangement, comprising:

a fixing assembly comprising a fixing rod and a handle, wherein the fixing rod is connected to the handle;

an ear spoon assembly which is arranged to be connected to the fixing rod for cleaning earwax;

a camera; and a light source, wherein the camera and the light source are assembled in the fixing rod.

In some embodiment, the fixing rod comprises a rod body and a light guide barrel extended from the rod body, wherein the camera and the light source are assembled in the rod body and the light guide barrel is positioned in front of the camera and the light source.

In some embodiment, the ear spoon assembly is detachably connected to the light guide barrel of the fixing rod, and the camera does not extend into the light guide barrel, thereby avoiding squeezing the camera during assembly of the ear spoon assembly on the light guide barrel.

In some embodiment, the ear spoon assembly comprises a rigid inner spoon and a flexible outer spoon, wherein the flexible outer spoon is adapted to be fitted to an outer side of the rigid inner spoon, and the rigid inner spoon comprises an annular installation part and an inner spoon body extended from the installation part, and the installation part of the rigid inner spoon is detachably connected to an outer surface of the light guide barrel.

In some embodiment, the camera comprises a lens end surface, wherein the flexible outer spoon comprises an end edge, and the rigid outer spoon has an end, wherein the center of the end of the rigid outer spoon is not coaxial with a center of the lens end surface of the camera, and after the flexible outer spoon is fitted to the outer side of the rigid inner spoon, a center position of the end edge of the flexible outer spoon is coaxial with the center of the lens end surface of the camera.

In some embodiment, the camera comprises a lens end surface, wherein the flexible outer spoon comprises a tip, and the rigid outer spoon has an end, wherein a center of the end of the rigid outer spoon is not coaxial with a center of the lens end surface of the camera, and after the flexible outer spoon is fitted to the outer side of the rigid inner spoon, a position of the tip of the flexible outer spoon is coaxial with the center of the lens end surface of the camera.

In some embodiment, the light source comprises a plurality of light emitting elements arranged around the camera, wherein the plurality of light emitting elements comprise two middle light emitting elements, wherein center positions of the two middle light emitting elements, the center of the lens end surface of the camera, and the center position of the end edge of the flexible outer spoon are located in a same plane.

In some embodiment, the light source comprises a plurality of light emitting elements arranged around the camera, wherein the plurality of light emitting elements comprise two middle light emitting elements, wherein center positions of the two middle light emitting elements, the center of the lens end surface of the camera, and the tip of the flexible outer spoon are located in a same plane In some embodiment, the fixing rod is made of thermally conductive material for dissipating heat generated when the camera and the light source are working, and thermal conductivity of the rigid inner spoon is lower than that of the fixing rod, thereby preventing heat from being transferred from the fixing rod to the inner spoon body of the rigid inner spoon.

In some embodiment, the camera comprises a lens end surface, wherein the ear spoon assembly comprises an ear spoon element, wherein the ear spoon element comprises an annular installation part and a spoon body component extended from the installation part, wherein the installation part is detachably connected to the light guide barrel, and a center position of an end of the spoon body component of the ear spoon element is coaxial with a center of the lens end surface of the camera.

In some embodiment, the ear spoon element is made of transparent material allowing light emitted from the light source to pass therethrough.

In some embodiment, the ear spoon element is formed by injection molding of two materials comprising an inner layer of polycarbonate and an outer layer of thermoplastic polyurethane elastomer.

In some embodiment, thermal conductivity of the ear spoon element is lower than that of the fixing rod, thereby preventing heat from being transferred from the fixing rod to the spoon body component of the ear spoon assembly.

In some embodiment, the camera comprises a lens end surface, wherein the ear spoon assembly comprises a rigid inner spoon and a flexible outer spoon comprising an en edge, wherein the rigid inner spoon is integrally extended from the light guide barrel, and a center position of the end edge of the flexible outer spoon is coaxial with a center of the lens end surface of the camera after the flexible outer spoon is fitted to an outer side of the rigid inner spoon.

In some embodiment, material of the rigid inner spoon is selected from one of metal, metal alloy, ceramic, plastic, and wood materials, and material of the flexible outer spoon is selected from silicone, thermoplastic polyurethane elastomer rubber, acrylonitrile-butadiene-styrene, polypropylene, polyimide, polyetherketone, polyvinyl chloride, ethylene-vinyl acetate copolymer, ethylene and α-olefin elastomer, one or more of thermoplastic elastomers.

In some embodiment, the camera comprises a lens end surface, wherein the light source comprises a light emitting surface that does not exceed the lens end surface of the camera.

In some embodiment, the fixing assembly comprises a holder which is assembled in the rod body for assembling the camera and the light source.

In some embodiments, the light guide barrel comprises an annular step surface at a position adjacent to the rod body, and the holder comprises an annular end surface which is suitable for fitting onto the step surface of the light guide barrel, wherein the inner surface of the holder and the inner surface of the light guide barrel form an integral inner wall to form a complete inner wall surface.

In some embodiments, the installation part comprises a plurality of positioning protrusions protruded from an inner surface thereof, and a positioning groove is formed between two adjacent the positioning protrusions, wherein the light guide barrel comprises a plurality of limiting protrusions, and a limiting groove is formed between two adjacent the limiting protrusions, wherein the installation part and the light guide barrel are capable of rotating with respect each other so that the positioning protrusions are respectively allowed to slide into the limiting grooves, and the positioning grooves engage with the limiting protrusions respectively, thereby allowing the installation part to be detachably connected to the light guide barrel.

In some embodiments, the positioning protrusions have an interference fit with the limiting grooves, and the positioning grooves have an interference fit with the limiting protrusions, wherein each the limiting groove has a sliding end which has a larger opening size than an opening size of a distal end thereof.

In some embodiments, the installation part comprises at least one positioning protrusion, wherein an outer surface of the light guide barrel forms at least one guide groove and a locking groove that extended laterally and communicated with the guide groove, wherein the at least one positioning protrusion is matched with the locking groove and is capable of entering the guide groove first and sliding into the locking groove when the installation part and the light guide barrel rotate relative to each other, thereby positioning the installation part on the light guide barrel.

In some embodiments, a detachable connection between the installation part and the fixing rod is selected from threaded connection, snap connection, magnetic attraction, and elastic engagement.

In some embodiments, the fixing assembly further comprises a transparent cover element which is located in front of the camera and the light source, and a waterproof layer bonding the transparent cover element to the rod body.

In some embodiments, material of the waterproof layer is selected from silicone sealant, epoxy resin sealant, polyurethane sealant, acrylic sealant, and butyl rubber adhesive.

In some embodiments, the transparent cover element has hydrophobicity, and a contact angle of the transparent cover element with water is greater than 90 degrees.

In some embodiments, the fixing assembly further comprises a transparent cover element which is a hydrophobic layer and is located on a front side of the camera and the light source.

In some embodiments, the light source comprises a light emitting surface, wherein the fixing assembly further comprises a waterproof layer which is a transparent layer covered on the light emitting surface of the light source, wherein the camera comprises a lens end surface, wherein the light emitting surface is located at a position behind the lens end surface of the camera in such a manner that the light source is arranged to project light beams from a rear side of the lend end surface of the camera.

In some embodiments, the fixing assembly further comprises a transparent cover element which is a hydrophobic layer and is attached to the lens end surface of the camera.

In some embodiments, an outer diameter of the installation part is the same as an outer diameter of the rod body, so that when the installation part is assembled on the outer surface of the light guide barrel, an outer surface of the installation part and an outer surface of the rod body are connected to form an integral cylindrical outer surface.

In some embodiments, the ear cleaning arrangement further comprises a display device, wherein the camera and the light source are electrically connected to the display device in a wired manner In some embodiments, the ear cleaning arrangement comprises a controller, which comprises a control circuit board, and the control circuit board is arranged to be communicatively connected to an electronic device in a wireless manner.

Still further objects and advantages will become apparent from a consideration of the ensuing description and drawings.

These and other objectives, features, and advantages of the present invention will become apparent from the following detailed description, the accompanying drawings, and the appended claims.

BRIEF DESCRIPTION OF THE DRAWINGS

FIG. 12 is a sectional view illustrating an ear spoon assembly and a fixing assembly of the ear cleaning arrangement according to the above second preferred embodiment of the present invention.

FIG. 13A is a sectional view illustrating the ear spoon assembly and the fixing rod of the ear cleaning arrangement according to the above second preferred embodiment of the present invention.

FIG. 13B is a partial enlarged schematic view illustrating the ear spoon assembly and the fixing rod of the ear cleaning arrangement according to the above second preferred embodiment of the present invention.

DETAILED DESCRIPTION OF THE PREFERRED EMBODIMENT

Figure 1:
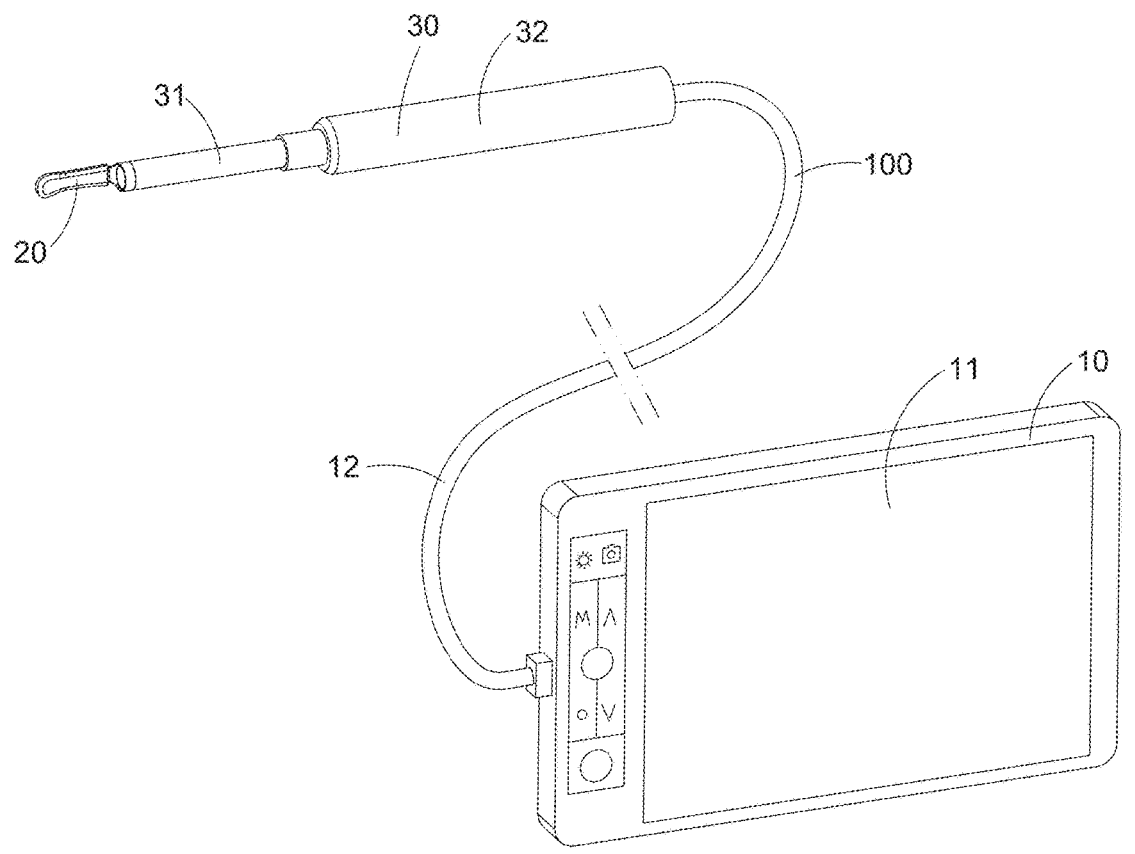
FIG. 1 is a perspective view of an ear cleaning arrangement according to a first preferred embodiment of the present invention.

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Those skilled in the art should understand that, in the disclosure of the present invention, terminologies of "longitudinal," "lateral," "upper," "front," "back," "left," "right," "perpendicular," "horizontal," "top," "bottom," "inner," "outer," and etc. that indicate relations of directions or positions are based on the relations of directions or positions shown in the appended drawings, which are only to facilitate descriptions of the present invention and to simplify the descriptions, rather than to indicate or imply that the referred device or element is limited to the specific direction or to be operated or configured in the specific direction. Therefore, the above-mentioned terminologies shall not be interpreted as confine to the present invention.

Referring to FIGS. 1 to 8 of the drawings, an ear cleaning arrangement 100 according to a first preferred embodiment of the present invention is provided for a user to perform ear cleaning operations on himself or herself or others such as children or the elderly. In the present invention, the ear cleaning arrangement 100 is exemplarily illustrated to be used for cleaning the user's own ear.

The ear cleaning arrangement 100 comprises a display device 10, an ear spoon assembly 20, a fixing assembly 30, a camera 40, and a light source 50. The display device 10 is communicated and connected to the camera 40, so that the camera 40 can capture images in the ear and display the images on the display device 10 for the user to observe the condition in their ear and locate the earwax. The ear spoon assembly 20 is connected to the fixing assembly 30 for cleaning the earwax in the ear. The fixing assembly 30 is connected to the display device 10. The camera 40 and the light source 50 are assembled in the fixing assembly 30. The light source 50 provides supplementary lighting for the camera 40 to illuminate the necessary positions in the ear, such as the auricle cavity and the ear canal, during the ear cleaning process.

The display device 10 comprises a display screen 11 and a connection wire 12. The display screen 11 is integrated with an image processor to process the image information sent by the camera 40, so as to display the images captured in the ear by the camera 40 in real time. This eliminates the need for the user to connect the ear cleaning arrangement 100 to other electronic devices, making it convenient for the user to use.

The connection wire 12 is used to connect the display screen 11 and the fixing assembly 30. It should be understood that the connection wire 12 comprises an outer sheath and electrical wires enclosed within the outer sheath. The electrical wires can be electrically connected to the camera 40 and the light source 50.

The display device 10 is also equipped with a power module which is electrically connected to the camera 40 and the light source 50 via the electrical wires, so as to provide power supply to the camera 40 and the light source 50. The power module can comprises a rechargeable battery, such as nickel-cadmium battery, nickel-hydrogen battery, lead-acid battery, lithium-ion battery, and lithium-polymer battery. The battery module can also be embodied to be connected to the municipal AC electricity supply, and the alternating current is converted into pulsating direct current by a rectifier for use by the display screen 11, the camera 40, and the light source 50.

The fixing assembly 30 comprises a fixing rod 31 and a handle 32. The fixing rod 31 is used to assemble the camera 40 and the light source 50, and the ear spoon assembly 20 is connected to the fixing rod 31. The handle 32 is connected to the fixing rod 31 for the user to hold, so that the user can hold the handle 32 to place the front end of the ear spoon assembly 20 into his or her ear for ear cleaning operations.

In this embodiment of the present invention, the fixing rod 31 is implemented as an internally hollow fixing barrel, and the camera 40 and the light source 50 are assembled into the fixing barrel. A diameter of the fixing rod 31 is smaller than that of the handle 32, and the handle 32 has a relatively larger diameter, which facilitates the user's grip and operation. The fixing rod 31 can be made of the same material as the handle 32 and my be integrally extended from the handle 32, or the fixing rod 31 and the handle 32 can be assembled and fixed together, such as by adhesive or screws.

The ear spoon assembly 20 in this embodiment is detachably connected to the fixing rod 31 of the fixing assembly 30, making it convenient for the user to replace the ear spoon assembly 20 of different sizes, so that the user can choose the suitable ear spoon assembly 20 for himself or herself. In other words, the present invention can provide ear spoon assemblies 20 of different sizes and styles for the user to choose and assemble on the fixing rod 31. After the ear spoon assembly 20 is detached from the fixing rod 31 of the fixing assembly 30, it can also be washed separately to avoid water entering the fixing assembly 30 and causing damage to the camera 40 and the light source 50.

As shown in FIGS. 2A to 4, the ear spoon assembly 20 comprises a rigid inner spoon 21 and a flexible outer spoon 22, and the flexible outer spoon 22 is detachably fitted on the rigid inner spoon 21. It can be understood that the rigid inner spoon 21 is made of rigid material such as metal, metal alloy, ceramic, plastic or wood. The flexible outer spoon 22 is made of flexible materials such as silicone, thermoplastic polyurethane elastomer rubber (TPU), Acrylonitrile-butadiene-styrene (ABS), polypropylene, polyimide, polyether ketone, polyvinyl chloride (PVC), ethylene-vinyl acetate copolymer (EVA), ethylene and alpha-olefin elastomer copolymer (POE), thermoplastic elastomer rubber (TPES) and other flexible plastics, which flexibly contact with the user's ear, thus will not scratch the user's ear.

The rigid inner spoon 21 comprises an installation part 211 and an inner spoon body 212, wherein the inner spoon body 212 is integrally extended from the installation part 211, and the flexible outer spoon 22 is sleeved on the inner spoon body 212. In this embodiment, the installation part 211 is in a barrel shape, and the inner spoon body 212 is integrally extended from a partial edge of the tubular installation part 211. The installation part 211 is used for being detachably assembled with the fixing rod 31.

As shown in FIGS. 2A to 4, the installation part 211 is sleeved on an outer surface of the fixing rod 31, so that the inner wall of the front end of the fixing rod 31 can remain smooth without the need to set a structure for being connected to the installation part 211. The detachable connection between the installation part 211 and the fixing rod 31 can have various possible forms, such as threaded connection, snap connection, magnetic attraction, etc. Alternatively, the installation part 211 is made of an elastic deformable material and can be tightly fitted to the front end of the fixing rod 31.

Figure 2A:
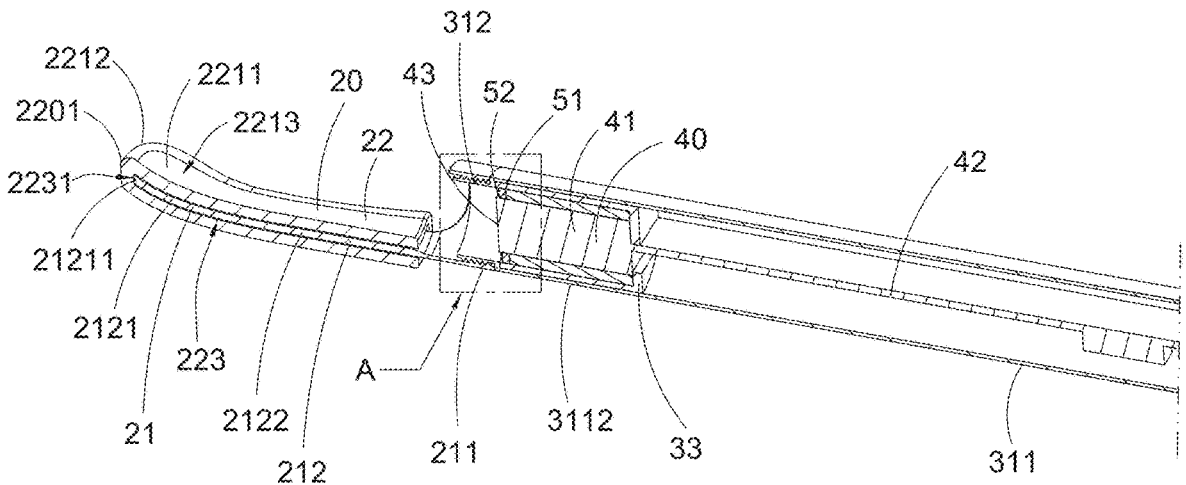
FIG. 2A is a sectional view illustrating an ear spoon assembly and a fixing rod of the ear cleaning arrangement according to the above first preferred embodiment of the present invention.
Figure 2B:
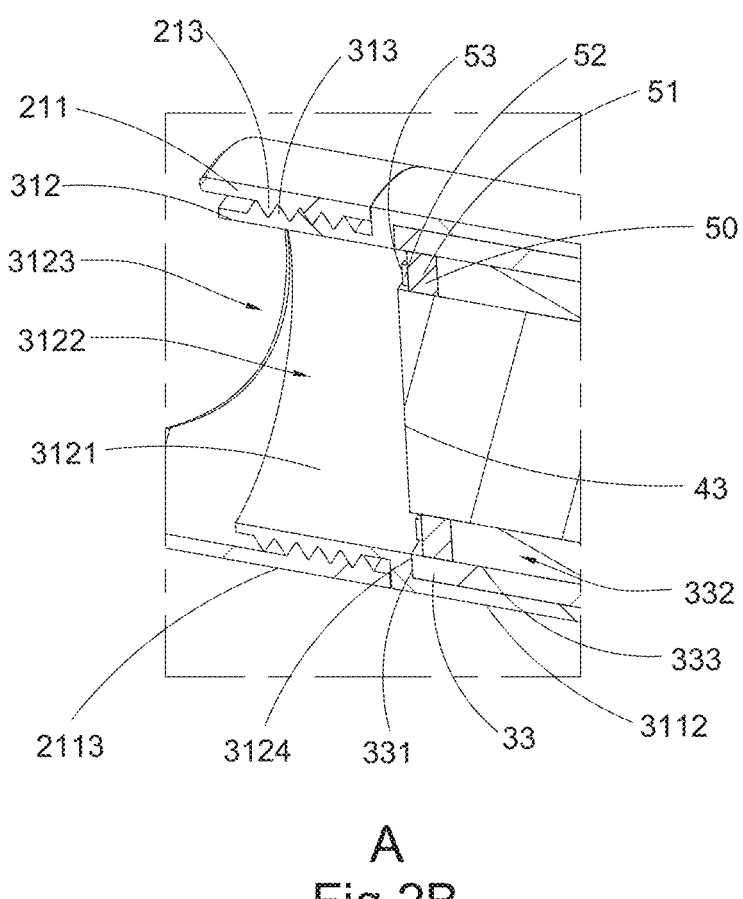
FIG. 2B is a partial enlarged view illustrating the ear spoon assembly and the fixing rod of the ear cleaning arrangement according to the above first preferred embodiment of the present invention.

More specifically, as shown in FIGS. 2A and 2B, the fixing rod 31 comprises a rod body 311 and a light guide barrel 312, wherein the light guide barrel 312 is integrally connected to the rod body 311, and the light guide barrel 312 is located in front of the camera 40 and the light source 50, thereby guiding the light emitted by the light source 50.

The rod body 311 in this embodiment can also form as a barrel, and a diameter of the light guide barrel 312 is smaller than a diameter of the rod body 311. The camera 40 is disposed in the rod body 311 without extending into the light guide barrel 312, and the light guide barrel 312 is also located in front of the light source 50. The light guide barrel 312 correspondingly forms a light guide wall 3121 on its inner wall, and the light guide wall 3121 forms a light guide channel 3122 and forms an opening 3123 communicating with the light guide channel 3122 at the front end. As a result, a portion of the light from the light source 50 can directly project into the ear through the opening 3123, and another portion of the light is reflected by the light guide wall 3121 and guided into the ear and project to an end of the ear spoon assembly 20 through the light guide channel 3122 and the opening 3123. Therefore, the light from the light source 50 is uniformly guided to the position that needs to be illuminated, and the light guide barrel 312 prevents external stray light from entering the field of view of the camera 40, thereby reducing glare or dark spots and providing the user with a clearer image on the display screen 11.

In other words, in this embodiment, the camera 40 and the light source 50 are not disposed at the corresponding position of the opening 3123, but are positioned in the fixing rod 31 away from the opening 3123, so that the light emitted by the light source 50 can be effectively directed into the field of view of the camera 40, and also avoid direct light from the external environment directly hitting the camera 40, so that the camera 40 can obtain clear image information of the corresponding opening 3123.

Figure 4:
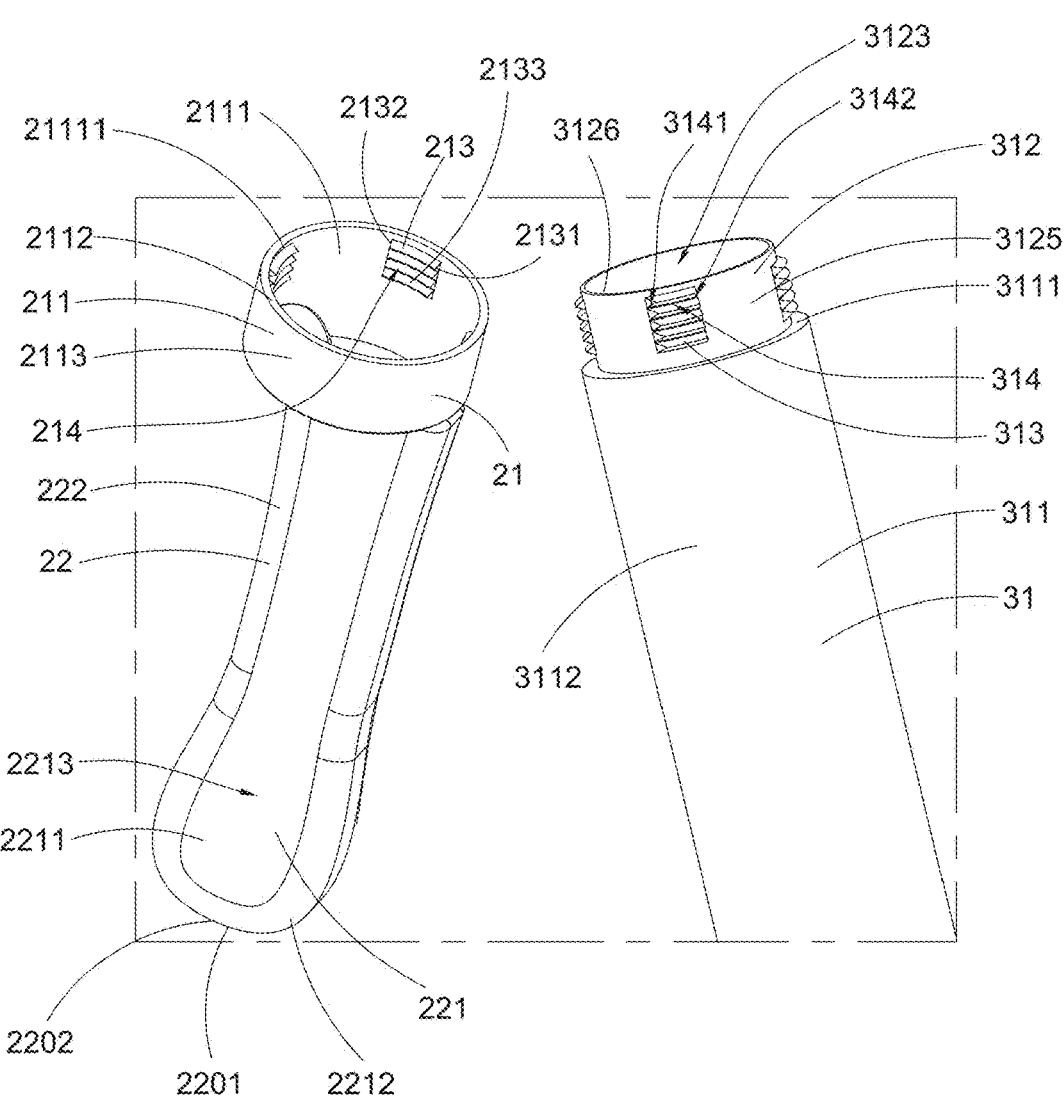
FIG. 4 is a perspective view illustrating the ear spoon assembly and the fixing rod of the ear cleaning arrangement according to the above first preferred embodiment of the present invention.
Figure 5:
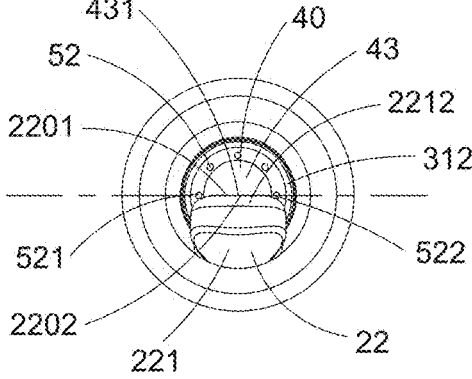
FIG. 5 is a schematic view illustrating the positional relationship between an end of the ear spoon assembly and a lens end surface of a camera of the ear cleaning arrangement according to the above first preferred embodiment of the present invention.

In addition, in this embodiment, the light guide barrel 312 is further used to be detachably connected with the installation part 211 of the rigid inner spoon 21. As shown in FIG. 4, the inner surface 2111 of the installation part 211 is locally provided with multiple sets of positioning protrusions 213 that are alternately spaced in the circumferential direction, and a positioning groove 214 is formed between two adjacent positioning protrusions 213. An outer surface 3125 of the light guide barrel 312 is locally provided with multiple sets of limiting protrusions 313 that are alternately spaced in the circumferential direction, and a limiting groove 314 is formed between two adjacent limiting protrusions 313. In the example shown in FIG. 4, each set of positioning protrusions 213 on an inner surface 2111 of the installation part 211 comprises four positioning protrusions 213 and forms three positioning grooves 214, and each set of limiting protrusions 313 on the outer surface 3125 of the light guide barrel 312 comprises five limiting protrusions 313 and forms four limiting grooves 314, thereby corresponding to the four positioning protrusions 213. The positioning protrusions 213 can slide correspondingly in the positioning grooves 214, and the limiting protrusions 313 can slide correspondingly in the positioning grooves 214, so as to detachably mount the installation part 211 of the rigid inner spoon 21 on the outer surface 3125 of the light guide barrel 312.

It can be understood that there is an interference fit between the protrusions and the grooves, so that after the installation part 211 of the rigid inner spoon 21 is assembled on the outer surface 3125 of the light guide barrel 312, the installation part 211 of the rigid inner spoon 21 can be tightly positioned on the outer surface 3125 of the light guide barrel 312 and not easily detached, thereby avoiding the ear spoon assembly 20 from falling off in the user's ear.

Each limiting groove 314 has an entrance 3141 with a gradually decreasing size from the opening towards the inside. A sliding end 2131 of the positioning protrusion 213 is guided into the limiting groove 314 through the entrance 3141 until a tail end 2132 of the positioning protrusion 213 reaches the entrance 3141 of the limiting groove 314, and the sliding end 2131 reaches an end 3142 of the limiting groove 314. Each positioning protrusion 213 tightly fits against the surface of the corresponding limiting groove 314, thereby tightly positioning the installation part 211 of the rigid inner spoon 21 on the outer surface 3125 of the light guide barrel 312. The groove width dimension of the end 3142 of the limiting groove 314 can be smaller, further limiting the maximum sliding displacement of the positioning protrusion 213 to prevent the positioning protrusion 213 from disengaging from the corresponding limiting groove 314.

As shown in FIG. 2B and FIG. 4, the cross-section of the limiting protrusion 313 is triangular, and the cross-section of the corresponding limiting groove 314 is also triangular. The cross-section of the positioning protrusion 213 is also triangular, thereby tightly fitting the surface of the positioning protrusion 213 with the surface of the corresponding limiting protrusion 313.

It can be understood that by setting the corresponding structure of the positioning protrusion 213 and the limiting protrusion 313, compared to the threaded connection method, it can be more stable and determine the assembly position of the installation part 211 of the rigid inner spoon 21 with the outer surface 3125 of the light guide barrel 312, thereby avoiding easy sliding of the installation part 211 of the rigid inner spoon 21 and the outer surface 3125 of the light guide barrel 312 in the axial direction as in the threaded connection method.

It is worth mentioning that the light guide barrel 312 is used to removably install the ear spoon assembly 20, and the camera 40 does not extend into the light guide barrel 312, thereby avoiding damage to the camera 40 due to compression during the installation of the installation part 211 of the rigid inner spoon 21 of the ear spoon assembly 20 onto the light guide barrel 312.

In addition, the rod body 311 of the fixing rod 31 has a circular top surface 3111 adjacent to the light guide barrel 312. The installation part 211 of the rigid inner spoon 21 has a circular bottom surface 2112 at the bottom end. When the installation part 211 of the rigid inner spoon 21 is assembled outside the light guide barrel 312, the circular bottom surface 2112 of the installation part 211 abuts against the circular top surface 3111 of the rod body 311, and the outer diameter of the circular installation part 211 is the same as the outer diameter of the rod body 311, so that the outer surface 2113 of the installation part 211 of the rigid inner spoon 21 is in contact with the outer surface 3112 of the rod body 311 to form a continuous columnar outer surface.

It is worth mentioning that, as shown in FIGS. 2A to 4, when the installation part 211 of the rigid inner spoon 21 is assembled outside the light guide barrel 312, a top edge 2133 of the positioning protrusion 213 of the installation part 211 is located below a top edge 3126 of the light guide barrel 312. In this way, the positioning protrusions 213 do not extend into the light path of the light source 50, avoiding the light emitted by the light source 50 from being projected onto the structure of the positioning protrusions 213 and generating stray light.

The length of the installation part 211 can be close to the length of the light guide barrel 312, thereby reducing the reflection of light emitted from the light source 50. The length of the installation part 211 can be slightly greater than the length of the light guide barrel 312, and its inner surface 2111 has a smooth top edge surface 21111, ensuring that the light guide barrel 312 is covered by the installation part 211, and the top edge surface 21111 is a smooth surface without the positioning protrusion 213, thereby not affecting the light path of the light source 50.

Figures 6, 7:
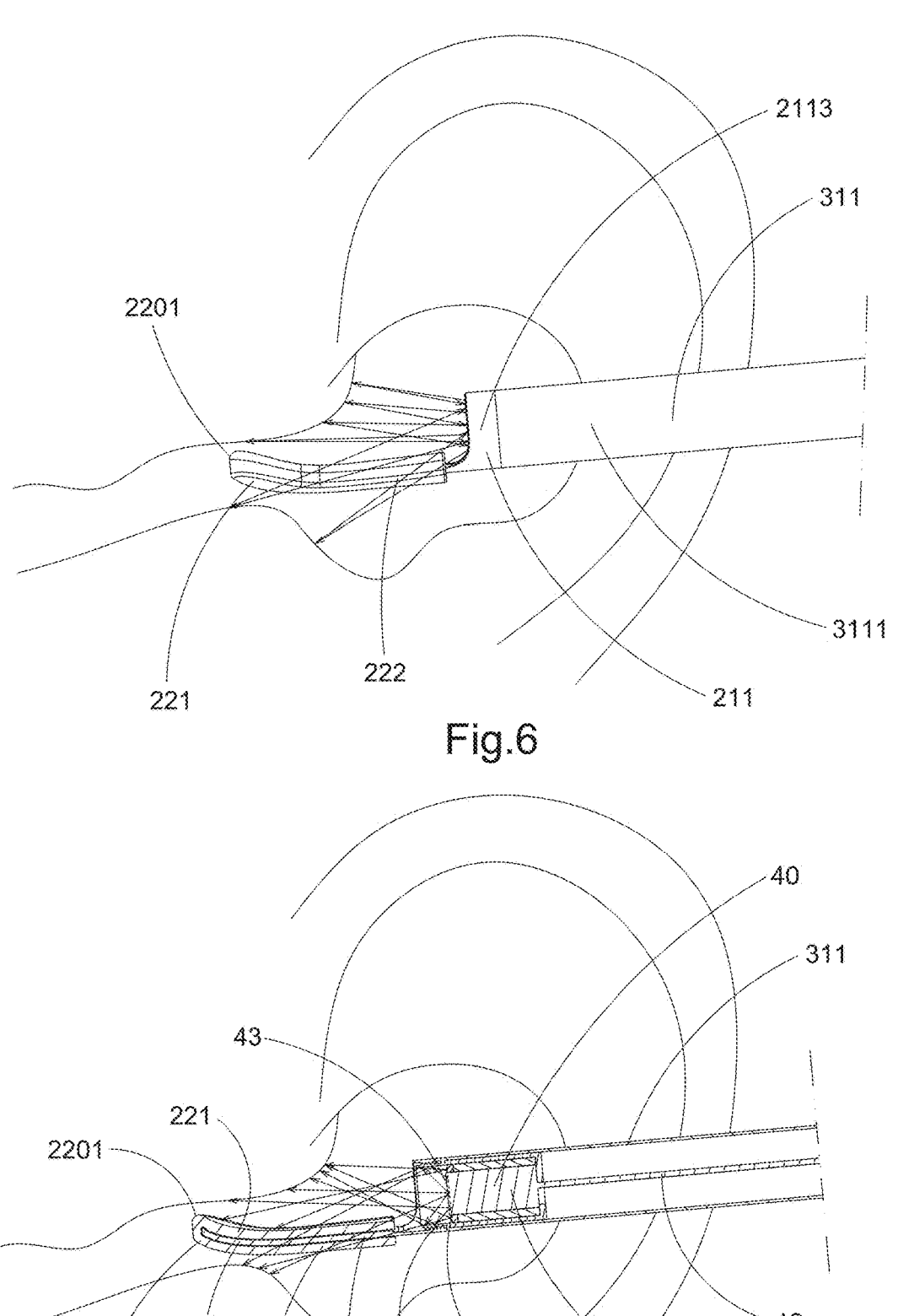
FIG. 6 is a schematic view illustrating the relationship between a human ear and the ear cleaning arrangement during operation according to the above first preferred embodiment of the present invention.
FIG. 7 is a schematic sectional view illustrating the relationship between the ear and the ear cleaning arrangement during operation according to the above first preferred embodiment of the present invention.

Correspondingly, the light guide wall 3121 of the light guide barrel 312 has excellent mirror reflection performance. For example, the material of the light guide barrel 312 is a material with high reflectivity, such as aluminum, nickel, silver, or the light guide barrel 312 is coated with aluminum film, nickel film, or silver film to form a mirror reflection surface on the light guide wall 3121. When the light emitted from the light source 50 is incident on the light guide wall 3121, it can be effectively reflected towards the opening 3123, and the light guide wall 3121 has good polishing performance, so that the light reflected from the ear to the light guide barrel 312 is reflected towards the camera 40 without causing stray light that affects the image effect, as shown in FIG. 6 and FIG. 7.

As shown in FIGS. 2A and 2B, the light source 50 comprises a light source circuit board 51 and a plurality of light emitting elements 52. The light source circuit board 51 is arranged around the camera 40 for installing the light emitting elements 52. The top of the light emitting elements 52 forms a light emitting surface 53. The camera 40 comprises a camera body 41 and a connection circuit board 42. The top of the camera body 41 forms a lens end surface 43. The light emitting surface 53 of the light source 50 is aligned with or located behind the lens end surface 43 of the camera 40, so that the light from the light source 50 is effectively emitted towards the opening 3123 of the light guide barrel 312 to illuminate the ear canal and the ear spoon assembly 20, thereby avoiding the generation of ineffective light directly towards the camera 40 and the generation of stray light from the side of the light source 50 that is directed towards the camera 40.

The light source circuit board 51 and the connection circuit board 42 can both be advantageously implemented as flexible circuit boards, which can be conveniently bent and extended in the fixing rod 31. The light source circuit board 51 and the connection circuit board 42 are electrically connected to each other and further connected to the display device 10, so that the camera 40 and the light source 50 can be controlled through the display device 10.

As shown in FIG. 2B, the fixing assembly 30 further comprises a holder 33 for installing the camera 40 and the light source 50. The light guide barrel 312 of the fixing rod 31 forms an annular step surface 3124 adjacent to the position of the handle 32. The holder 33 comprises an annular end surface 331, which is adhered to the step surface 3124 by adhesive to assemble the holder 33 in the handle 32. The holder 33 also forms a receiving cavity 332 for accommodating the camera 40. The connection circuit board 42 can pass through the holder 33, so as to be electrically connect to the display device 10.

Preferably, an inner surface 333 of the holder 33 has the same inner diameter as the light guide wall 3121 of the light guide barrel 312. When the annular end surface 331 of the holder 33 is adhered to the step surface 3124, the inner surface 333 of the holder 33 and the light guide wall 3121 of the light guide barrel 312 form a continuous tubular inner wall, which is used to guide and reflect the light emitted by the light source 50.

Figure 3:
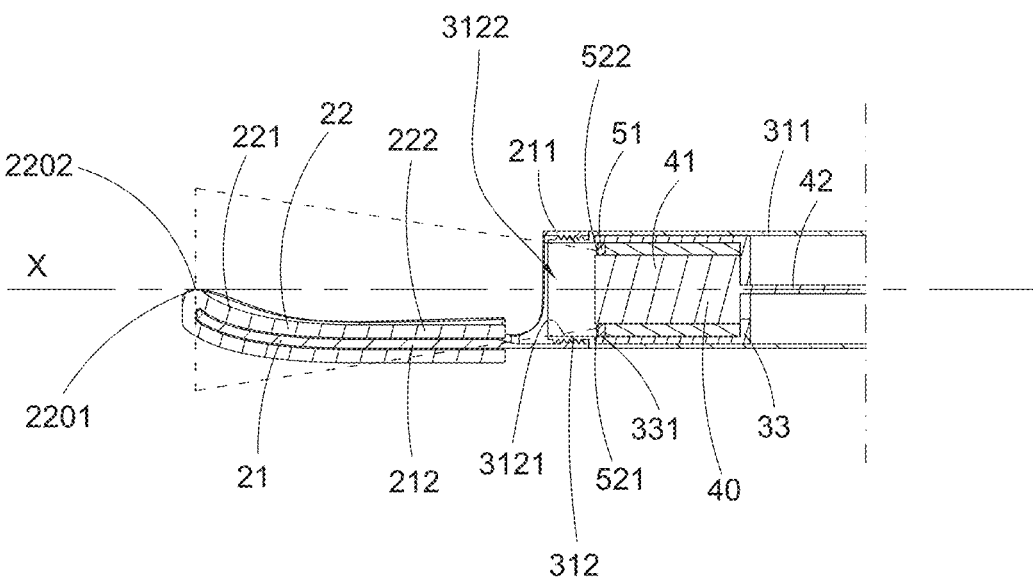
FIG. 3 is a sectional view illustrating the ear spoon assembly and a light guide barrel being in an assembled state according to the above first preferred embodiment of the present invention.

As shown in FIG. 3, the flexible outer spoon 22 is detachably fitted outside the rigid inner spoon 21, and an end edge 2201 of the flexible outer spoon is used to contact and clean the earwax, and a center position 2202 is coaxial with a center 431 of the lens end surface 43 of the camera 40, that is, coaxial with the central axis X of the camera 40, so that the user can accurately judge the position of the end edge 2201 of the flexible outer spoon 22 in the image and facilitate the user to operate the ear cleaning arrangement 100 to clean the earwax accurately, and avoid scratching the ear canal and causing infection by the ear spoon assembly 20.

The light emitting elements 52 of the light source 50 are evenly distributed around the camera 40, and these light emitting elements 52 comprise two middle light emitting elements 521 and 522 located at two ends of the diameter of the lens end surface 43 of the camera 40, that is, the two light emitting elements located on the left and right sides of the lens end surface 43. The light emitting center positions of these two middle light emitting elements 521 and 522 are in the same straight line as the central end face 431 of the lens 43 of the camera 40, and also is in the same plane with the end of the ear spoon assembly 20, that is, the end edge 2201 of the flexible outer spoon 22, so as to ensure that the center of the end of the ear spoon assembly 20 and the earwax in the ear are in the center of the field of view of the camera 40, making it easier for the user to operate the ear spoon assembly 20 to aim at and clean the earwax.

That is to say, the two middle light emitting elements 521 and 522 respectively emit light, so that the earwax appearing in the field of view of the camera 400 is exactly located at the center position of the end of the ear spoon assembly 20 in the field of view, rather than on a position deviated from the center. Therefore, in the circular image field of view of the display device 10, when the earwax image is displayed in the center of the image field of view, the user can precisely aim at and clean the earwax using the center position 2202 of the end edge 2201 of the flexible outer spoon 22.

As shown in FIGS. 2A to 4, the flexible outer spoon 22 comprises a flexible spoon body 221 and an extension part 222, wherein the flexible spoon body part 221 is integrally extended from the extension part 222. The flexible spoon body part 221 comprises a spoon bottom 2211 and a flange part 2212 that is integrally extended from the spoon bottom 2211. The flange part 2212 and the spoon bottom 2211 form a groove 2213 for accommodating earwax. The end of the flange part 2212 forms the end edge 2201 of the flexible outer spoon 22, and the end edge 2201 of the flexible outer spoon 22 is parallel and coplanar with the two middle light emitting elements 521 and 522, and the center position 2202 of the end edge 2201 is coaxial with the center 431 of the lens end surface 43 of the camera 40.

The flexible outer spoon 22 has an installation channel 223 which extends in the extension part 222 and the flexible spoon body part 221 for installing the rigid inner spoon 21. The inner spoon body 212 of the rigid inner spoon 21 comprises a rigid spoon body 2121 and a connection part 2122. The connection part 2122 is integrally extended from the installation part 211, and the rigid spoon body 2121 is integrally extended from the connection part 2122.

The rigid spoon body 2121 of the inner spoon body 212 of the rigid inner spoon 21 has an end 21211. When the end 21211 of the rigid spoon body 2121 abuts against the end 2231 of the installation channel 223 of the flexible outer spoon 22, the end edge 2201 of the flange part 2212 of the flexible spoon body part 221 is precisely positioned at the center 2202 of the end edge 2201 and the center 431 of the lens end surface 43 of the camera 40, and is in the same plane as the center positions of the two middle light emitting elements 521 and 522 and the center 431 of the lens end surface 43 of the camera 40.

Figure 8:
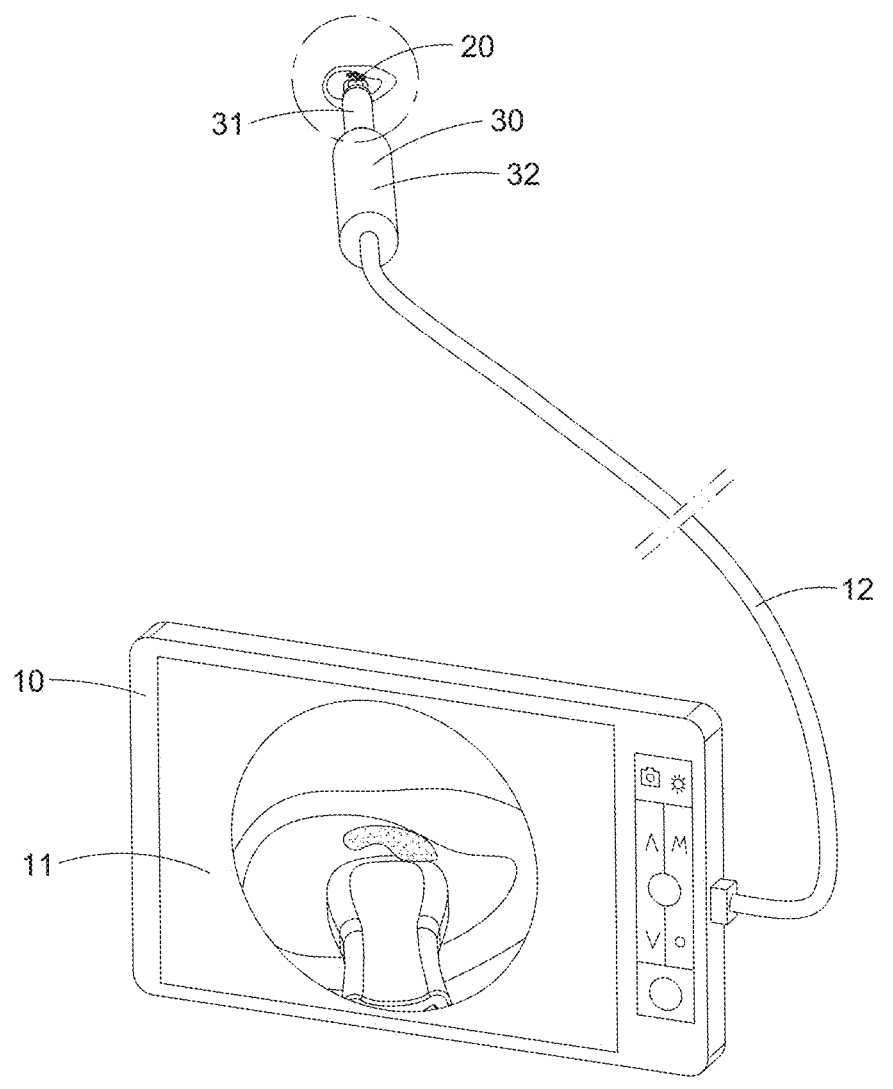
FIG. 8 is a perspective view of the ear cleaning arrangement during operation according to the above first preferred embodiment of the present invention.

As shown in FIG. 8, the user can hold the handle 32 to guide the end 2201 of the ear spoon assembly 20 into their ear, and the light emitted by the light source 50 is projecting into the ear. The camera 40 captures the image of the flexible outer spoon 22 of the ear spoon assembly 20 and the inside of the ear, and displays it on the display screen 11 of the display device 10. The end 2201 of the flexible outer spoon 22 of the ear spoon assembly 20 is located at the center of the circular image field of view, making it convenient to scrape the earwax in the ear into the groove 2213 of the flexible spoon body part 221 and clean it out of the ear along with the ear spoon assembly 20.

Referring to FIGS. 9 to 25, an ear cleaning arrangement 100 according to a second preferred embodiment of the present invention is illustrated to comprise an ear spoon assembly 20, a fixing assembly 30, a camera 40, a light source 50, and a controller 60. In this embodiment of the present invention, the ear cleaning arrangement 100 can be wirelessly connected to an electronic device 1 such as a mobile phone, tablet, etc., so that the user can watch the real-time image of the inside of the ear captured by the camera 40 on the electronic device 1.

In this embodiment, the ear spoon assembly 20 is connected to the fixing assembly 30 for cleaning earwax in the ear. The camera 40, the light source 50, and the controller 60 are assembled within the fixing assembly 30. The light source 50 provides supplementary lighting for the camera 40 to illuminate the areas in the ear that need to be illuminated during the ear cleaning process, such as the ear canal and the earlobe cavity.

Correspondingly, the controller 60 is communicatively connected to the electronic device 1, which means that the controller 60 can be embodied to comprises a control circuit board 61 which is integrated with a wireless communication module, such as a cellular network module, WiFi module, Bluetooth module, or ZigBee module, etc. Thus, the electronic device 1 can wirelessly obtain the image information captured by the camera 40 of the ear cleaning arrangement 100.

The controller 60 is also equipped with a power module 62 which is electrically connected to the control circuit board 61 and further connected to the camera 40 and the light source 50, so s to provide power supply to the camera 40 and the light source 50. The power module 62 may include a rechargeable battery, including but not limited to nickel-cadmium battery, nickel-hydrogen battery, lead-acid battery, lithium-ion batteries, lithium polymer battery.

The fixing assembly 30 comprises a fixing rod 31 and a handle 32. The fixing rod 31 is used to assemble the camera 40 and the light source 50, and the ear spoon assembly 20 is connected to the fixing rod 31. The handle 32 is connected to the fixing rod 31 to accommodate the control circuit board 61 and the power module 62 of the controller 60, and to be held by the user's hand. Thus, the user can hold the handle 32 to place the front end of the ear spoon assembly 20 into their ear for ear cleaning operations.

Figure 9:
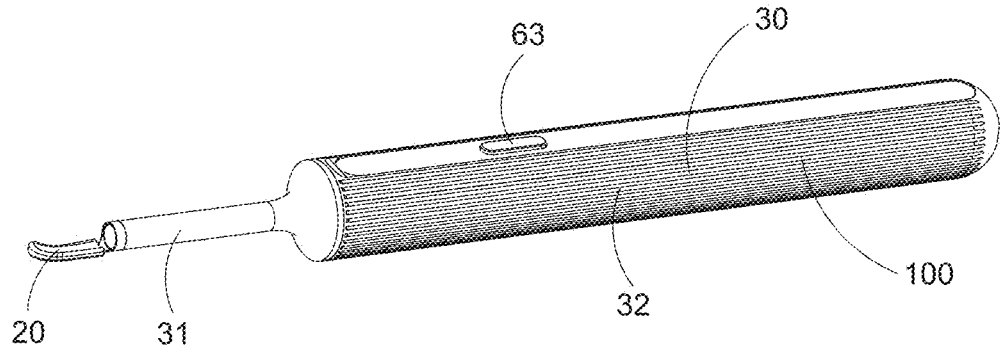
FIG. 9 is a perspective view of an ear cleaning arrangement according to a second preferred embodiment of the present invention.
Figures 10, 11:
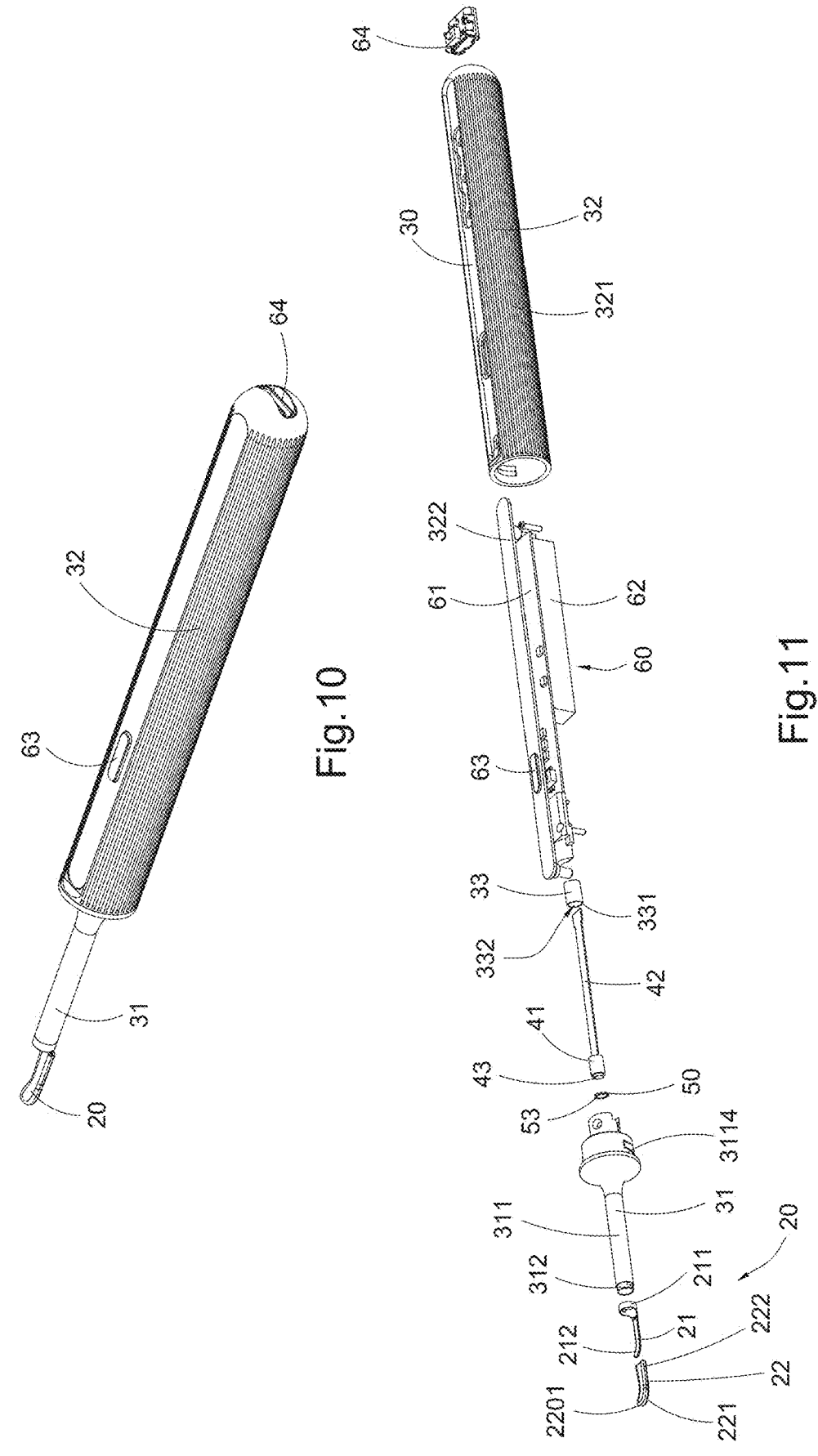
FIG. 10 is another perspective view of the ear cleaning arrangement according to the above second preferred embodiment of the present invention.
FIG. 11 is an exploded view of the ear cleaning arrangement according to the above second preferred embodiment of the present invention.

The controller 60 also comprises a control switch 63, which can be implemented as a button or a knob. As shown in FIGS. 9 to 11, a button is shown as an example and is assembled on the handle 32 to be exposed externally for the user to press. The controller 60 also comprises a charging interface 64, which is electrically connected to the power module 62, so that the rechargeable battery in the power module 62 can be charged when being connected to an external power source.

As shown in FIGS. 11 to 12, in this embodiment, the handle 32 comprises a handle body 321 and a cover 322. A receiving chamber 323 is formed in the handle body 321, and the cover 322 is assembled on the handle body 321 to provide a flat surface for printing product identification. The receiving chamber 323 is used to accommodate the control circuit board 61 and the power module 62.

In this embodiment of the present invention, the fixing rod 31 is implemented as an internally hollow fixing barrel. The camera 40 and the light source 50 are disposed in the fixing barrel. The diameter of the fixing rod 31 is smaller than that of the handle 32, and the handle 32 has a relatively larger diameter, making it convenient for the user to grip and operate. In this embodiment, the fixing rod 31 is assembled and fixed with the handle 32, such as by adhesive bonding or using screws and other components.

The ear spoon assembly 20 in this embodiment can be detachably connected to the fixing rod 31 of the fixing assembly 30, so as to facilitate the user to replace the ear spoon assembly 20 of different sizes for the user to select the suitable ear spoon assembly 20. For example, it can be selected from the ear spoon assembly 20 shown in FIGS. 9 to 17, FIGS. 18 to 20, or FIGS. 22 to 23.

As shown in FIGS. 13A to 15, the ear spoon assembly 20 comprises a rigid inner spoon 21 and a flexible outer spoon 22, wherein the flexible outer spoon 22 is detachably fitted onto the rigid inner spoon 21. It can be understood that the rigid inner spoon 21 is correspondingly made of rigid material. The flexible outer spoon 22 is made of flexible material and flexibly contacts with the user's ear, so as not to scratch the user's ear.

The rigid inner spoon 21 comprises an installation part 211 and an inner spoon body 212, wherein the inner spoon body 212 is integrally extended from the installation part 211, and the flexible outer spoon 22 is sleeved on the inner spoon body 212. In this embodiment, the installation part 211 is annular, and the inner spoon body 212 is integrally extended from a partial edge of the annular installation part 211. The installation part 211 is used for being detachably assembled with the fixing rod 31.

More specifically, as shown in FIGS. 11 to 14, the fixing rod 31 comprises a rod body 311 and a light guide barrel 312, wherein the light guide barrel 312 is integrally connected with the rod body 311, and the light guide barrel 312 is located in front of the camera 40 and the light source 50, so as to guide the light emitted by the light source 50. The rod body 311 comprises a connecting end 3114, which is suitable for insertion or adhesion to the front end of the handle 32, thereby assembling the fixing rod 31 with the handle 32.

The rod body 311 in this embodiment can also form with a tubular structure, and the diameter of the light guide barrel 312 is smaller than the diameter of the rod body 311. The camera 40 is disposed in the rod body 311 without extending into the light guide barrel 312, and the light guide barrel 312 is also located in front of the light source 50. The light guide barrel 312 correspondingly forms a light guide wall 3121 on its inner wall, and the light guide wall 3121 forms a light guide channel 3122 and forms an opening 3123 communicating with the light guide channel 3122 at the front end. As a result, a portion of the light from the light source 50 can directly project into the ear through the opening 3123, and another portion of the light is reflected by the light guide wall 3121 and guided into the ear and the end of the ear spoon assembly 20 through the light guide channel 3122 and the opening 3123. Therefore, the light from the light source 50 is uniformly guided to the position that needs to be illuminated, and the light guide barrel 312 prevents external stray light from entering the field of view of the camera 40, thereby reducing glare or dark spots and providing the user with a clearer image on the display screen 11.

Figure 15:
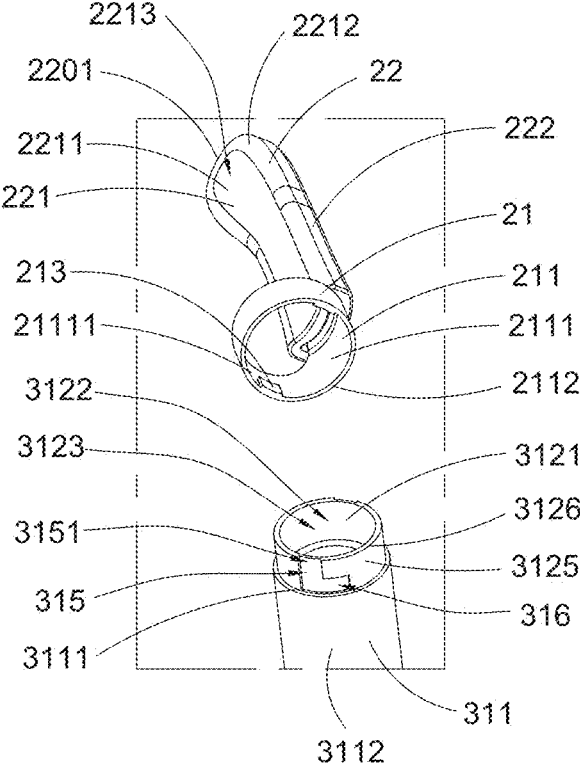
FIG. 15 is a perspective view illustrating the ear spoon assembly and fixing rod of the ear cleaning arrangement according to the above second preferred embodiment of the present invention.

In addition, in this embodiment, the light guide barrel 312 is further used to detachably assemble the installation part 211 of the rigid inner spoon 21. As shown in FIG. 15, the outer surface 3125 of the light guide barrel 312 is formed with one or more fixing groove structures comprising a longitudinal guide groove 315 and a locking groove 316 extending transversely from a bottom of the guide groove 315. The inner surface 2111 of the installation part 211 of the rigid inner spoon 21 is provided with one or more positioning protrusions 213, which correspond in shape and size to the locking groove 316 and correspond in size to the notch 3151 at a top of the guide groove 315, so that each positioning protrusion 213 is suitable for entering the notch 3151 at the top of the guide groove 315 and then laterally entering the locking groove 316, thereby being limited in the locking groove 316 to assemble the installation part 211 of the rigid inner spoon 21 on the outside of the light guide barrel 312.

More specifically, during the assembly process of the installation part 211 of the rigid inner spoon 21 onto the outer surface 3125 of the light guide barrel 312, the ear spoon assembly 20 is first slid along the longitudinal direction, i.e., the length direction of the fixing rod 31, onto the outer surface of the light guide barrel 312. Each positioning protrusion 213 is aligned with the notch 3151 at the top end of the guide groove 315, so that the positioning protrusion 213 can slide in the guide groove 315. When each positioning protrusion 213 reaches the bottom end of the guide groove 315, the installation part 211 is rotated so that the positioning protrusion 213 enters the locking groove 316. Preferably, the corresponding positioning protrusion 213 and the locking groove 316 are further interference fitted, so that the positioning protrusion 213 is not easily detached from the fixed groove structure, thereby securely positioning the ear spoon assembly 20 on the outer surface 3125 of the light guide barrel 312.

It can be understood that by setting the corresponding positioning protrusion 213 with the guide groove 315 and the locking groove 316, the structure can be more stable compared to the threaded connection method, and the assembly position of the installation part 211 of the rigid inner spoon 21 with the outer surface 3125 of the light guide barrel 312 can be determined, thus avoiding the easy sliding of the installation part 211 of the rigid inner spoon 21 with the outer surface 3125 of the light guide barrel 312 along the axial direction in a similar threaded connection method.

The light guide barrel 312 is used to detachably install the ear spoon assembly 20. The camera 40 does not extend into the light guide barrel 312, thereby avoiding damage to the camera 40 due to compression during the installation of the rigid inner spoon 21 of the ear spoon assembly 20 in the installation part 211 of the light guide barrel 312.

In addition, the rod body 311 of the fixing rod 31 has a circular top surface 3111 near the light guide barrel 312, and the installation part 211 of the rigid inner spoon 21 has a circular bottom surface 2112 at the bottom. When the installation part 211 of the rigid inner spoon 21 is assembled outside the light guide barrel 312, the circular bottom surface 2112 of the installation part 211 abuts against the circular top surface 3111 of the rod body 311, and the outer diameter of the circular installation part 211 is the same as the outer diameter of the rod body 311, thereby forming a continuous columnar outer surface where the outer surface 2113 of the installation part 211 of the rigid inner spoon 21 is in contact with the outer surface 3112 of the rod body 311.

It is worth mentioning that, as shown in FIG. 15, the guide groove 315 and the locking groove 316 are concavely provided on the outer surface 3125 of the light guide barrel 312 without penetrating the light guide barrel 312. When the installation part 211 is assembled on the light guide barrel 312, the positioning protrusion 213 is set on the bottom inner surface of the inner surface 2111 of the installation part 211 and adjacent to the bottom opening of the annular installation part 211. In this way, the top edge 213 is located below the top edge 3126 of the light guide barrel 312, so that the positioning protrusion 213 does not extend into the optical path of the light source 50, thereby avoiding the structure of the positioning protrusion 213 from causing stray light when the light emitted by the light source 50 is projected onto the positioning protrusion 213.

The length of the installation part 211 can be close to the length of the light guide barrel 312, thereby reducing the reflection of light emitted from the light source 50. The length of the installation part 211 can be slightly greater than the length of the light guide barrel 312, and its inner surface 2111 has a smooth top edge surface 21111 located above the positioning protrusion 213, ensuring that the light guide barrel 312 is covered by the installation part 211, and the top edge surface 21111 is a smooth surface without the positioning protrusion 213, thereby not affecting the light path of the light source 50.

Correspondingly, the light guide wall 3121 of the light guide barrel 312 has excellent mirror reflection performance. For example, the material of the light guide barrel 312 is a highly reflective material such as aluminum, nickel, silver, or the light guide barrel 312 is coated with a film such as aluminum film, nickel film, or silver film to form a mirror reflection surface on the light guide wall 3121. Therefore, when the light emitted by the light source 50 is incident on the light guide wall 3121, it can be effectively reflected towards the opening 3123, and the light guide wall 3121 has good polishing performance, so that the light reflected from the ear to the light guide barrel 312 will not form stray light that affects the image effect when it is reflected to the camera 40.

As shown in FIG. 13A to FIG. 13B, the light source 50 comprises a light source circuit board 51 and a plurality of light emitting elements 52. The light source circuit board 51 surrounds the camera 40 for installing the light emitting elements 52. The top of the light emitting elements 52 forms a light emitting surface 53. The camera 40 comprises a camera body 41 and a connection circuit board 42. The top of the camera body 41 forms a lens end surface 43. The light emitting surface 53 of the light source 50 is aligned with or located behind the lens end surface 43 of the camera 40, so that the light from the light source 50 is effectively emitted towards the opening 3123 of the light guide barrel 312 to illuminate the ear canal and the ear spoon assembly 20, thereby avoiding the formation of ineffective light directly towards the camera 40 and also avoiding the side reflection of light from the light source 50 towards the camera 40.

The light source circuit board 51 and the connection circuit board 42 can both preferably be implemented as flexible circuit boards, so that they can conveniently extend and bend in the fixing rod 31, and the light source circuit board 51 and the connection circuit board 42 are electrically connected and further electrically connected to the control circuit board 61 of the controller 60, so that the camera 40 and the light source 50 can be controlled by the switch element 63.

Figure 14:
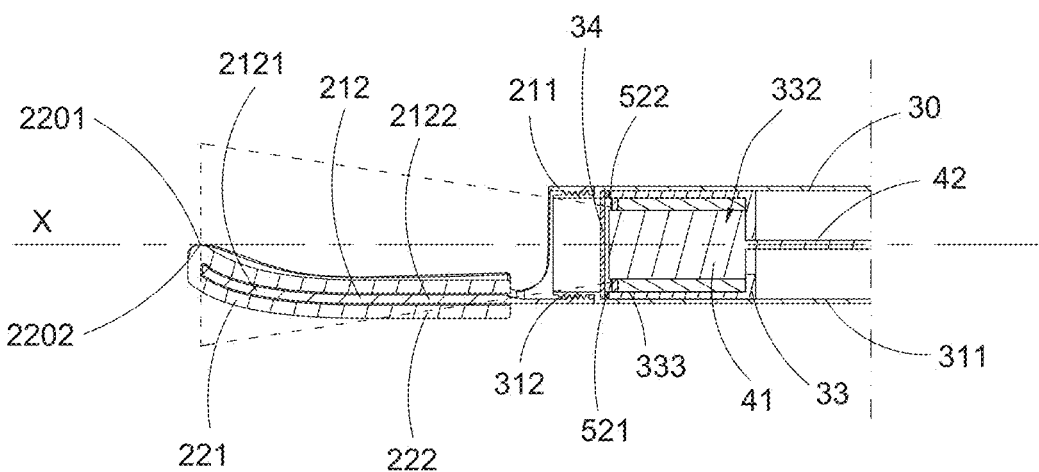
FIG. 14 is a sectional view illustrating the ear spoon assembly being assembled with a light guide barrel of the ear cleaning arrangement according to the above second preferred embodiment of the present invention.

As shown in FIGS. 13A to 14, the fixing assembly 30 further comprises a holder 33 for installing the camera 40 and the light source 50. The light guide barrel 312 of the fixing rod 31 forms an annular step surface 3124 adjacent to the handle 32. The holder 33 comprises an annular end surface 331, which is adhered to the step surface 3124 by adhesive to assemble the holder 33 in the handle 32. The holder 33 also forms a receiving cavity 332 for accommodating the camera 40. The connection circuit board 42 can pass through the holder 33 to electrically connect to the control circuit board 61.

Preferably, the inner surface 333 of the holder 33 has the same inner diameter as the light guide wall 3121 of the light guide barrel 312. When the annular end surface 331 of the holder 33 is adhered to the step surface 3124, the inner surface 333 of the holder 33 and the light guide wall 3121 of the light guide barrel 312 form a continuous tubular inner wall, which is used to guide and reflect the light emitted by the light source 50.

The holder 33 and the fixing rod 31 can be made of a thermally conductive material to dissipate heat to the environment through the outer surface of the fixing rod 31, thereby avoiding heat transfer to the ear spoon assembly 20 and keeping the ear spoon assembly 20 at a relatively low temperature. Alternatively, the fixing rod 31 can be made of a thermal insulating material, and the heat generated by the camera 40 and the light source 50 during operation is transferred to the handle 32 through the connection circuit board 42, thereby dissipating heat at the position of the handle 32 to avoid heat transfer to the ear spoon assembly 20.

The rigid inner spoon 21 of the ear spoon assembly 20 and the fixing rod 31 can be made of the same material, or the rigid inner spoon 21 and the fixing rod 31 can be made of different materials. For example, the rigid inner spoon 21 can be made of a plastic material with lower thermal conductivity compared to the fixing rod, so that the rigid inner spoon 21 prevents the heat generated by the camera 40 and the light source 50 during operation from being transferred to the end of the ear spoon assembly 20 via the fixing rod 31.

In addition, the connection circuit board 42 is a flexible circuit board located in the fixing rod 31 and can be bent and extended for easy extension in the fixing rod 31.

The fixing assembly 30 further comprises a transparent sealing element 34, which is adhered to the holder 33 through a waterproof layer 35 to serve as a transparent cover for sealing the camera 40 and the light source 50, and can be fitted to the light guide barrel 312 of the fixing rod 31 to form a circular step surface 3124 adjacent to the handle 32. The waterproof layer 35 comprises but is not limited to silicone sealant, epoxy resin sealant, polyurethane sealant, acrylic sealant, butyl rubber adhesive, etc. Preferably, for the convenience of manufacturing process, the waterproof layer 35 can be UV-curable adhesive. In this way, when the fixing rod 31 is cleaned or during the cleaning process of the ear spoon assembly 20, if water enters the light guide barrel 312, the waterproof layer 35 further prevents water from entering the rod body 311, thereby avoiding damage to the camera 40, the light source 50, and the control circuit board 61.

It is worth mentioning that the transparent sealing element 34 preferably further has hydrophobic properties, with a contact angle with water greater than 90 degrees. This means that after the ear cleaning arrangement 100 is cleaned with water, if water enters the light guide barrel 312, water droplets will not remain on the transparent sealing element 34. Therefore, the user does not need to wait for the water to evaporate before immediately using the ear cleaning arrangement 100, thus avoiding wasting the user's time.

It can be understood that the hydrophobic material of the transparent sealing element 34 can include, but is not limited to, polyurethane compounds, polyimide compounds, organosilane compounds, fluorocarbon compounds, fluorinated ether polymers, fluorosilane compounds, fluoroacrylate compounds, methyltrimethoxysilane, propyltrimethoxysilane, vinyltriethoxysilane, isopropyltri(dioctylphosphato) titanate, tribenzyl citrate, titanium dioxide hydrogenated silicon carbon nitrogen oxide film, etc.

Figure 18:
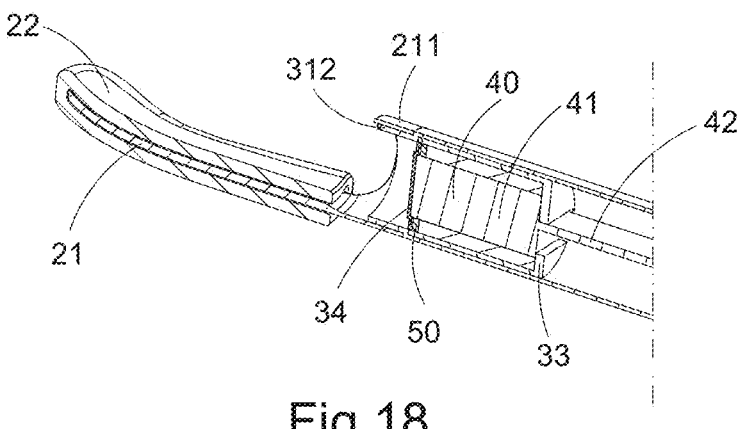
FIG. 18 is a sectional schematic diagram showing a deformation embodiment of the transparent cover element of the ear cleaning arrangement according to the above second preferred embodiment of the present invention.

As shown in FIG. 18, according to another embodiment, the transparent sealing element 34 can also be a layer of coating, which is a hydrophobic layer and is coated on the outer surface of the camera 40 and the light source 50.

As shown in FIG. 14, the flexible outer spoon 22 is detachably fitted over the rigid inner spoon 21, and the end edge 2201 of the flexible outer spoon is used to contact and clean the earwax, and the center position 2202 is coaxial with the central end face 431 of the lens 43 of the camera 40, that is, coaxial with the central axis X of the camera 40, so that the user can accurately determine the position of the end edge 2201 of the flexible outer spoon 22 in the image and facilitate the user to operate the ear cleaning arrangement 100 to clean the earwax accurately, and avoid scratching the ear canal and causing infection by the ear spoon assembly 20.

The light emitting elements 52 of the light source 50 are evenly distributed around the camera 40, and these light emitting elements 52 include two middle light emitting elements 521 and 522 located at the two ends of the diameter of the lens end surface 43 of the camera 40, that is, the two light emitting elements shown to be located on the left and right sides of the lend end surface 43. The light emitting points of these two middle light emitting elements 521 and 522 are on the same straight line as the central end face 431 of the lens 43 of the camera 40, and is also in the same plane with the end of the ear spoon assembly 20, that is, the end edge 2201 of the flexible outer spoon 22, thereby ensuring that the center of the end of the ear spoon assembly 20 and the earwax in the ear are in the center of the field of view of the camera 40, making it easier for the user to operate the ear spoon assembly 20 to aim at the earwax for cleaning.

That is to say, the two middle light emitting elements 521 and 522 respectively emit light, so that the earwax appearing in the field of view of the camera 400 is exactly located at the center position of the end of the ear spoon assembly 20, rather than on a position deviated from the center. Therefore, in the circular image field of view of the electronic device 1, when the earwax image is displayed in the center of the image field of view, the user can use the center position 2202 of the end edge 2201 of the flexible outer spoon 22 to precisely aim at and clean the earwax.

As shown in FIGS. 12 to 15, the flexible outer spoon 22 comprises a flexible spoon body 221 and an extension part 222, wherein the flexible spoon body part 221 is integrally extended from the extension part 222. The flexible spoon body part 221 comprises a spoon bottom 2211 and a flange part 2212 that integrally protrudes and extends from the spoon bottom 2211. The flange part 2212 and the spoon bottom 2211 form a groove 2213 for accommodating earwax. The end of the flange part 2212 forms the end edge 2201 of the flexible outer spoon 22, and the end edge 2201 of the flexible outer spoon 22 is parallel and coplanar with the two middle light emitting elements 521 and 522, and the center position 2202 of the end edge 2201 is coaxial with the center 431 of the lens end surface 43 of the camera 40.

The flexible outer spoon 22 has an installation channel 223 which is extended in the extension part 222 and the flexible spoon body part 221 for installing the rigid inner spoon 21. The inner spoon body 212 of the rigid inner spoon 21 comprises a rigid spoon body 2121 and a connection part 2122. The connection part 2122 is integrally extended from the installation part 211, and the rigid spoon body 2121 is integrally extended from the connection part 2122.

The rigid spoon body 2121 of the inner spoon body 212 of the rigid inner spoon 21 has an end 21211. When the end 21211 of the rigid spoon body 2121 abuts against the end 2231 of the installation channel 223 of the flexible outer spoon 22, the end edge 2201 of the flange part 2212 of the flexible spoon body part 221 is precisely positioned at the center 2202 of the end edge 2201 and the center 431 of the lens end surface 43 of the camera 40, and is in the same plane as the center positions of the two middle light emitting elements 521 and 522 and the center 431 of the lens end surface 43 of the camera 40.

Figure 16:
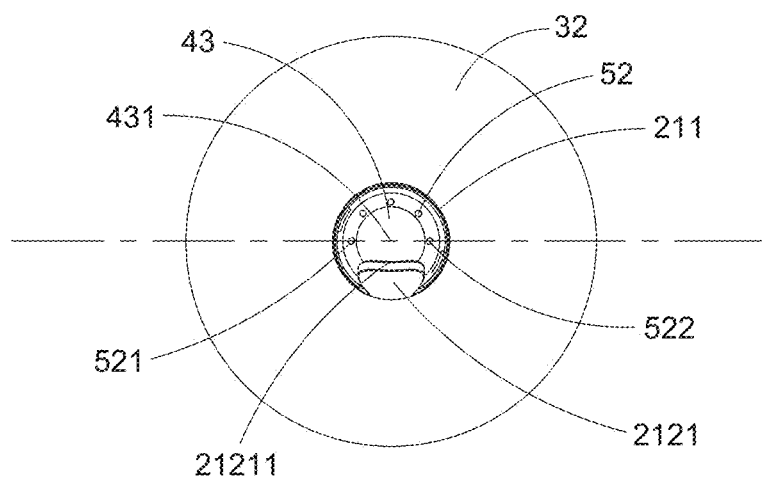
FIG. 16 is a schematic view illustrating the positional relationship between an end of the rigid inner spoon of the ear spoon assembly and a center of a lens end surface of the camera of the ear cleaning arrangement according to the above second preferred embodiment of the present invention.

As shown in FIG. 16, the end 21211 of the rigid spoon body 2121 is not coaxial with the center 431 of the lens end surface 43 of the camera 40. As shown in the drawings, when the flexible outer spoon 22 is set on the rigid inner spoon 21, the end edge 2201 of the flange part 2212 of the flexible spoon body part 221 is exactly positioned at the center position 2202 of the end edge 2201, coaxial with the center 431 of the lens end surface 43 of the camera 40.

Figure 17:
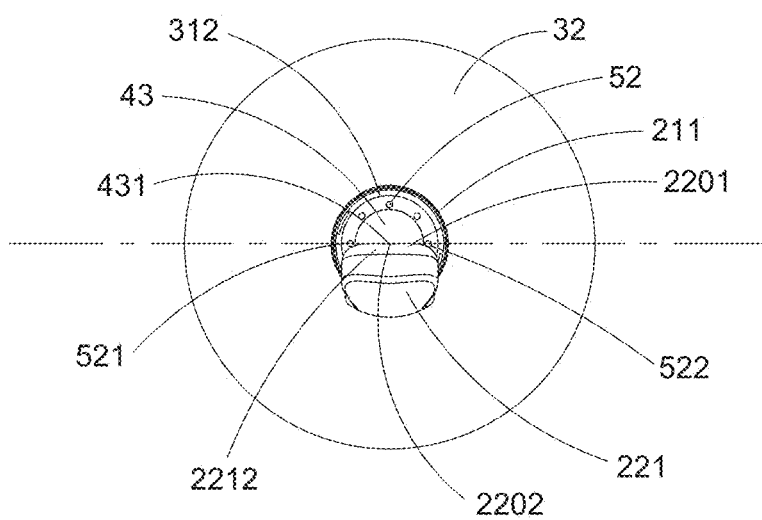
FIG. 17 is a schematic view illustrating the positional relationship between an end of a flexible outer spoon of the ear spoon assembly and the center of the lens end surface of the camera of the ear cleaning arrangement according to the above second preferred embodiment of the present invention.

As shown in FIG. 17, the flexible spoon body part 221 of the flexible outer spoon 22 is offset from the central axis X of the camera 40, so that the center position 2202 of the end edge 2201 is coaxial with the center 431 of the lens end surface 43 of the camera 40. The rigid spoon body 2121 is offset towards the central axis X of the camera 40 to support the flexible spoon body part 221 of the flexible outer spoon 22.

Figure 19:
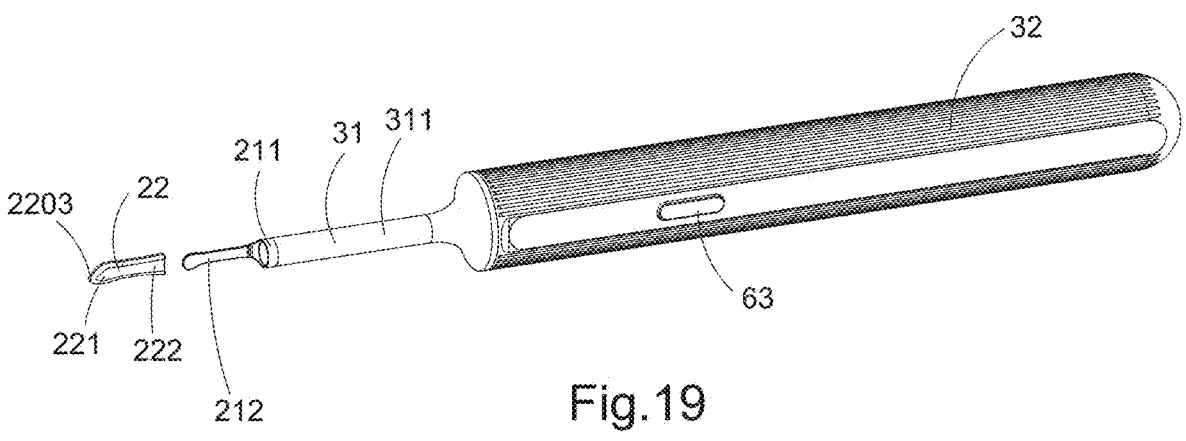
FIG. 19 is a schematic view illustrating the ear cleaning arrangement with a first alternative ear spoon assembly according to the above second preferred embodiment of the present invention.
Figure 20:
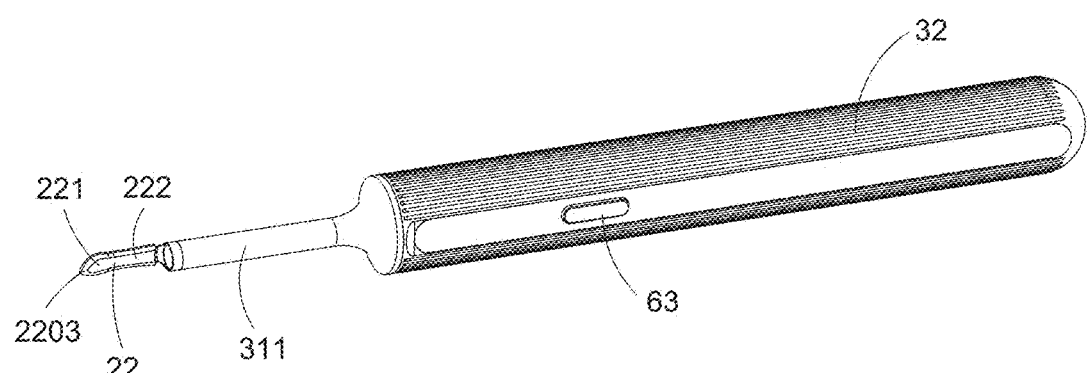
FIG. 20 is a perspective view of the ear cleaning arrangement with the first alternative ear spoon assembly according to the above second preferred embodiment of the present invention.
Figure 21:
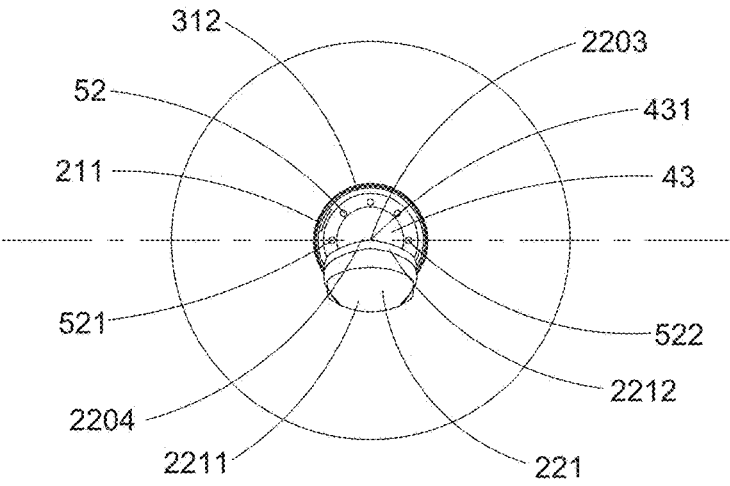
FIG. 21 is a schematic view illustrating the positional relationship between a flexible outer spoon of the first alternative ear spoon assembly and a center of the lens end surface of a camera of the ear cleaning arrangement according to the above second preferred embodiment of the present invention.

As shown in FIGS. 19 to 21, according to an alternative mode, the flexible outer spoon can be constructed in a different shape. Specifically, the flexible spoon body 221 of the flexible outer spoon 22 forms a tip 2203, and the flexible spoon body part 221 gradually increases in size from a tip 2203 towards the extension part 222, forming a curved transition surface 2204. That is, the flexible spoon body part 221 does not have the aforementioned edge 2201, and the tip 2203 forms the center position 2202 of the end of the flexible spoon body part 221. The tip 2203 is coaxial with the center 431 of the lens end surface 43 of the camera 40, that is, it is coaxial with the center axis X of the camera 40, so that the user can accurately determine the position of the tip 2203 of the flexible outer spoon 22 in the image and facilitate the user to operate the ear cleaning arrangement 100 to clean the earwax accurately, avoiding scratching the ear canal and causing infection with the ear spoon assembly 20.

In addition, the center positions of the light emitting points of the two middle light emitting elements 521 and 522 of the light source 50 are in the same line as the center 431 of the lens end surface 43 of the camera 40, and are in the same plane as the tip 2203 of the flexible outer spoon 22, thereby ensuring that the center of the end of the ear spoon assembly 20 and the earwax in the ear are located at the center of the field of view of the camera 40.

Figure 22:
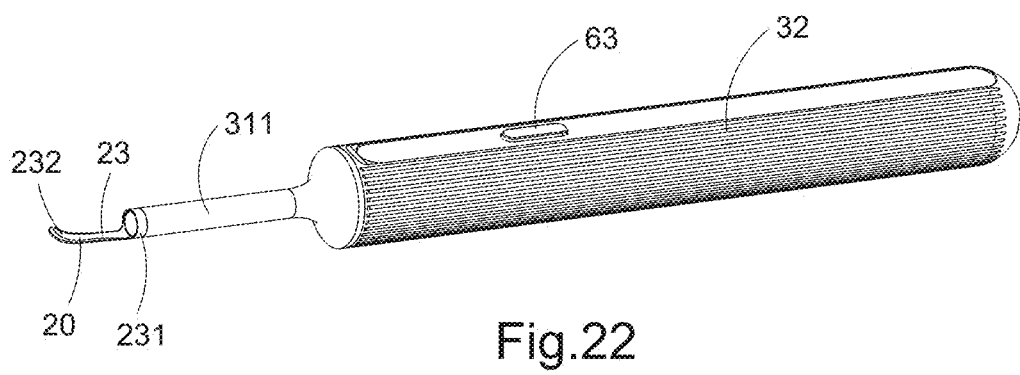
FIG. 22 is a perspective view of the ear cleaning arrangement with a second alternative ear spoon assembly according to the above second preferred embodiment of the present invention.
Figure 23:
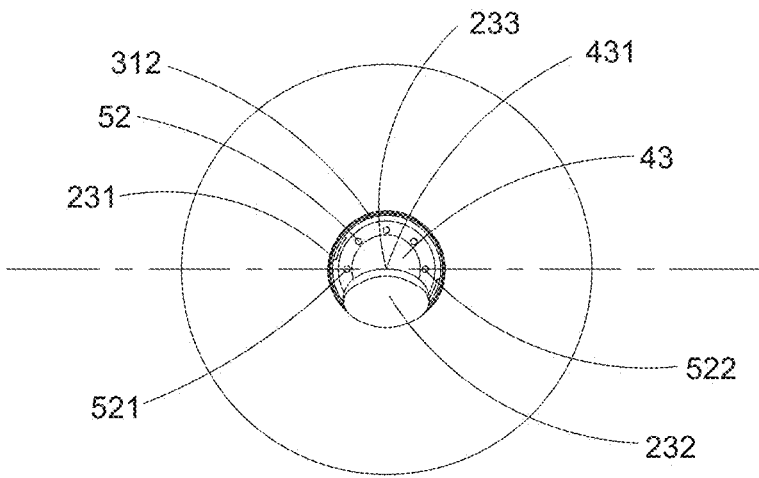
FIG. 23 is a schematic view illustrating the positional relationship between an end of a spoon element of the second alternative ear spoon assembly and a center of the lens end surface of a camera of the ear cleaning arrangement according to the above second preferred embodiment of the present invention.

As shown in FIG. 22 to FIG. 23, according to another alternative mode, the ear spoon assembly 20 comprises an ear spoon element 23 which comprises an installation part 231 and a spoon body component 232. In this embodiment, unlike the ear spoon assembly 20 described in the above embodiment which comprises an inner spoon and an outer spoon, the ear spoon element 23 only has a single component, wherein the installation part 231 can be constructed with a detachable connection structure such as a thread, a buckle, or the structure of the positioning projection and the positioning groove as described in the above embodiment, so as to be detachably assembled on the light guide barrel 312.

In this embodiment, the ear spoon element 23 is made of transparent plastic material, so that the light emitted by the light source 50 will not be blocked by the ear spoon element 23, thereby obtaining more image information in the human ear. That is to say, in the above embodiment, when the rigid inner spoon 21 is made of, for example, a metal material, the position corresponding to the local part of the ear where the rigid inner spoon 21 is located cannot be captured by the camera 40, while in the present invention, the image information of the position in the ear in front of the ear spoon element 23 can also be captured by the camera 40.

Preferably, the ear spoon element 23 is formed by injection molding of an outer layer of thermoplastic polyurethane elastomer rubber and an inner layer of polycarbonate (PC) fluid material, so that it can achieve a moderate softness and hardness. The polycarbonate material provides a predetermined hardness while the thermoplastic polyurethane elastomer rubber ensures the flexibility of the ear spoon element 23, thereby preventing the ears from being scratched and infected while ensuring the scraping effect of the ear spoon element 23.

In addition, the ear spoon element 23 and the fixing rod 31 can be made of different materials. For example, the ear spoon element 23 can be made of a material with poorer thermal conductivity than the fixing rod 31, so that the ear spoon element 23 prevents the heat generated during the operation of the camera 40 and the light source 50 from being transferred to the end of the ear spoon element 23 via the fixing rod 31, causing a burning sensation in the user's ear.

As shown in FIG. 23, a center position 233 of the end of the ear spoon element 23 is coaxial with the center position 431 of the lens end surface 43 of the camera 40, that is, coaxial with the central axis X of the camera 40, so that the user can accurately determine the position of the center position 233 of the end of the ear spoon element 23 in the image and facilitate the user to operate the ear cleaning arrangement 100 to clean the earwax accurately, and avoid scratching the ear canal and causing infection.

In addition, the center positions of the two middle light emitting elements 521 and 522 of the light source 50 are on the same line as the center position 431 of the lens end surface 43 of the camera 40, and are in the same plane as the center position 233 of the end of the ear spoon element 23, so as to ensure that the center position of the end of the ear spoon assembly 20 and the earwax in the ear are in the center of the field of view of the camera 40.

Figure 24:
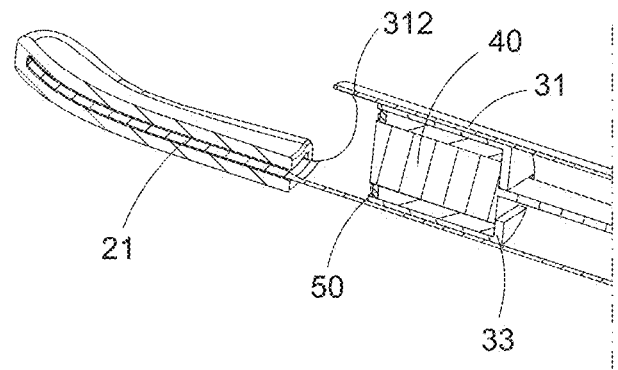
FIG. 24 is a sectional view of the ear cleaning arrangement with a third alternative ear spoon assembly according to the above second preferred embodiment of the present invention.
Figures 25, 26:
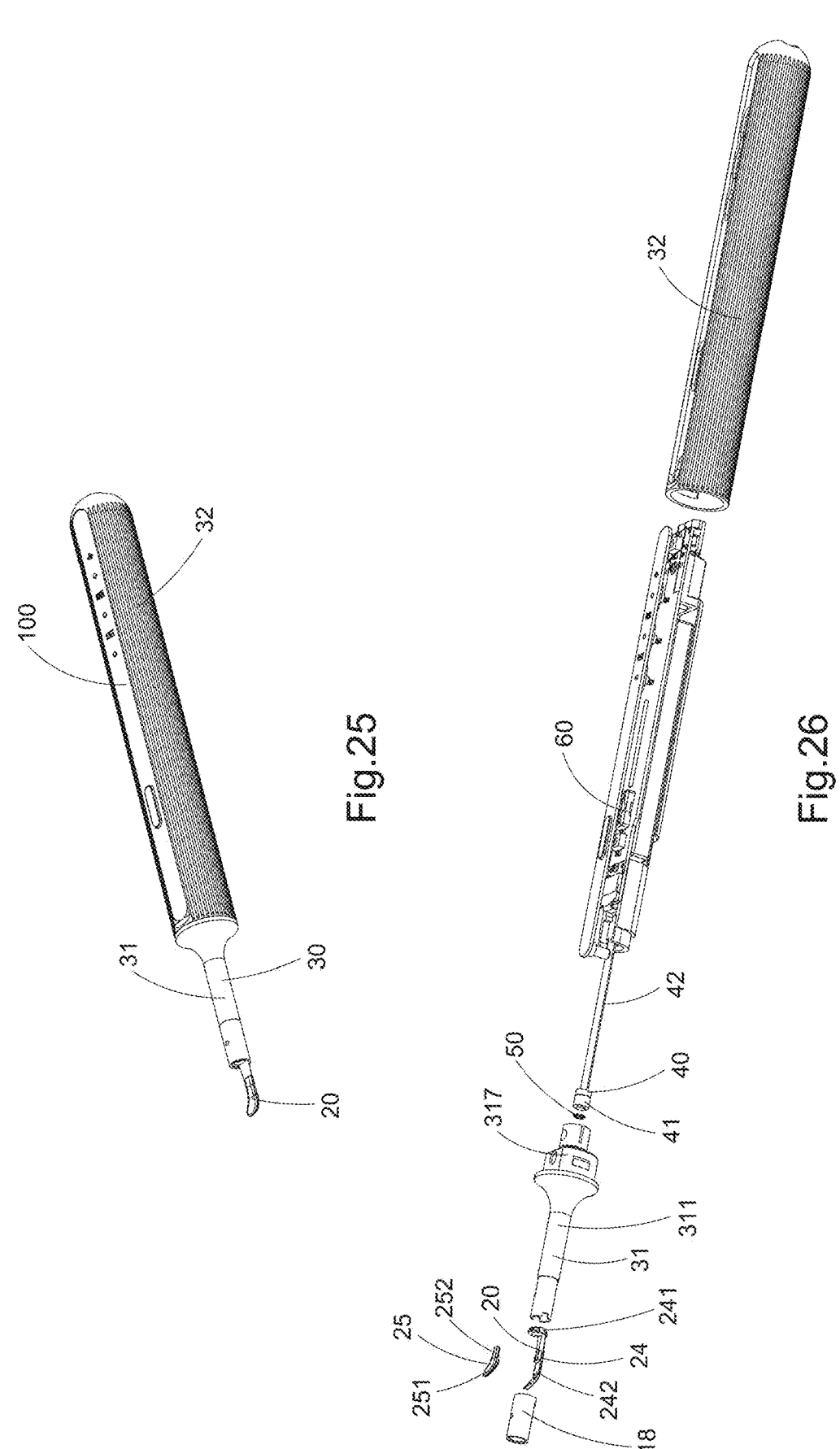
FIG. 25 is a perspective view of an ear cleaning arrangement according to a fourth alternative mode the above second preferred embodiment of the present invention.
FIG. 26 is an exploded view of the ear cleaning arrangement according to the fourth alternative mode of the above second preferred embodiment of the present invention.
Figure 27:
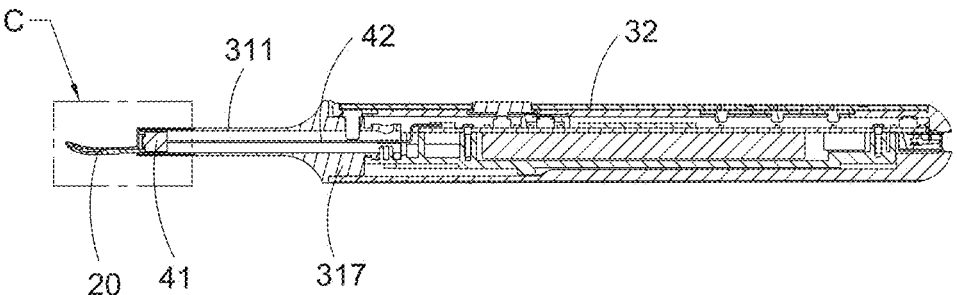
FIG. 27 is a sectional view of the ear cleaning arrangement according to the fourth alternative mode of the above second preferred embodiment of the present invention.
Figure 28:
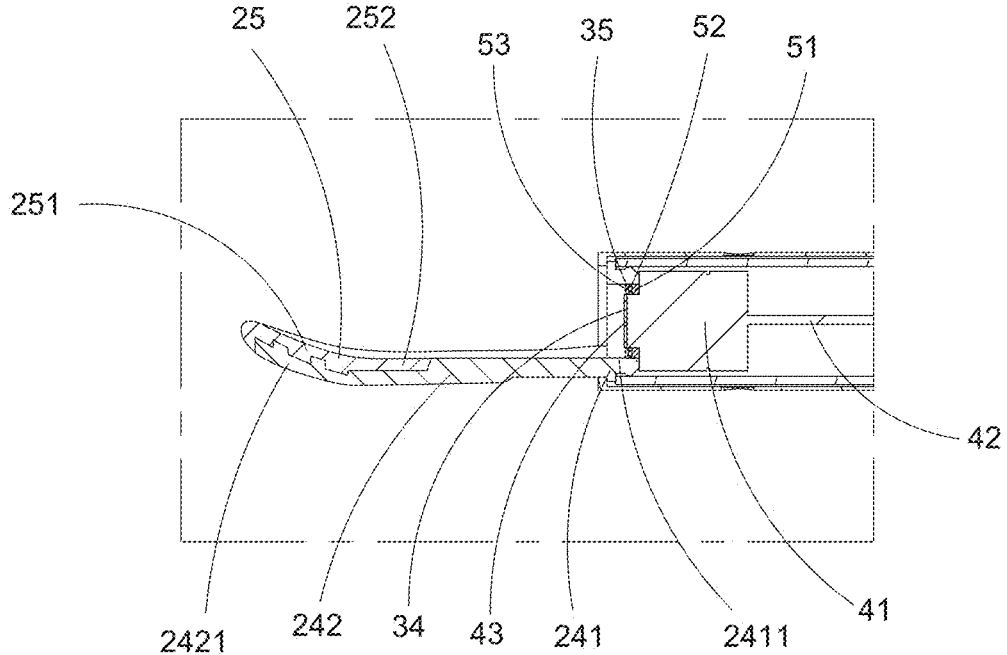
FIG. 28 is a partial enlarged schematic view illustrating the installation of a camera and a light source assembly of the ear cleaning arrangement according to the fourth alternative mode of the second preferred embodiment of the present invention.

As shown in FIG. 24, according to another alternative mode, the rigid inner spoon 21 of the ear spoon assembly 20 can be integrally connected to the light guide barrel 312, so that the rigid inner spoon 21 is integrally fixed to the fixing rod 31 and cannot be disassembled.

As shown in FIGS. 25 to 28, an ear cleaning arrangement 100 according to another alternative mode of the above second preferred embodiment comprises an ear spoon assembly 20, a fixing assembly 30, a camera 40, a light source 50, and a controller 60. In this embodiment of the present invention, the ear cleaning arrangement 100 can be wirelessly connected to an electronic device 1 such as mobile phone and tablet computer, so that the user can view the image in the ear captured by the camera 40 in real time on the electronic device 1.

In this embodiment, the ear spoon assembly 20 comprises a rigid spoon seat 24 and a flexible spoon 25 which is installed above the rigid spoon seat 24 to come into contact with the user's ear. In other words, unlike the previous embodiment, the flexible outer spoon 22 is not fitted over the rigid inner spoon 21. In this embodiment, the flexible spoon 25 is stacked on top of the rigid spoon seat 24.

Correspondingly, as shown in the drawings the rigid spoon seat 24 comprises an installation part 241 and a spoon seat body 242, wherein the spoon seat body 242 is integrally extended from the installation part 241, and the installation part 241 is connected to the fixing assembly 30. The flexible spoon 25 comprises a flexible spoon body part 251 and an extension part 252, wherein the flexible spoon body part 251 is integrally extended from the extension part 252. The spoon seat body 242 comprises an inclined extension rigid spoon body part 2421, and the flexible spoon body part 251 of the flexible spoon 25 is installed on the inclined rigid spoon body part 2421, so that the flexible spoon body part 251 extends inwardly for easy ear cleaning operation.

In this embodiment, the fixing assembly 30 comprises a fixing rod 31 and a handle 32. The rod 31 comprises a rod body 311 and a sleeve 318. The rod body 311 is used to install the camera 40 and the light source 50. In this embodiment, the rigid spoon seat 24. The installation part 241 is extended into the rod body 311 to form a light guide barrel 2411, and the light guide barrel 2411 is located in front of the camera 40 and the light source 50. The installation part 241 of the rigid spoon seat 24 is mounted on the light guide barrel 313, and the sleeve 318 is sleeved on the outer side of the light guide barrel 312 and the installation part 241.

As shown in the drawings, the light source 50 comprises a light source circuit board 51 and a plurality of light emitting elements 52. The light source circuit board 51 surrounds the camera 40 for installing the light emitting elements 52. The top of the light emitting elements 52 forms a light emitting surface 53. The camera 40 comprises a camera body 41 and a connection circuit board 42. The top of the camera body 41 forms a lens end surface 43. The light emitting surface 53 of the light source 50 is located behind the lens end surface 43 of the camera 40, so that the light from the light source 50 can effectively be emitted towards the opening 3123 of the light guide barrel 312 to illuminate the ear canal and the ear spoon assembly 20, thereby avoiding the generation of ineffective light directly towards the camera 40 and avoiding the side reflection of light from the light source 50 towards the camera 40.

In addition, a waterproof layer 35 is provided on the light emitting surface 53 of the light source 50. In the manufacturing process, the waterproof layer 35 is coated on the entire light emitting surface 53 of the light source 50 to fix and install the light source 50. The waterproof layer 35 is a transparent layer and can be implemented as a UV-curable adhesive, which facilitates dispensing and curing without affecting the light emission effect of the light source 50 after curing.

It is worth mentioning that, because the waterproof layer 35 needs to be set on the light emitting surface 53 of the light source 50, the light emitting surface 53 of the light source 50 is located behind the lens end surface 43 of the camera 40. Therefore, when applying glue on the light emitting surface 53 of the light source 50, the fluid-like waterproof layer 35 will not be applied to the lens end surface 43 of the camera 40, so as not to affect the shooting effect of the camera 40.

In this embodiment, a transparent sealing element 34 with a hydrophobic structure is also set on the lens end surface 43 of the camera 40. In this way, after the ear cleaning arrangement is washed with water, water droplets are not easily left on the front of the camera 40, so that the ear cleaning arrangement can be used in a timely manner without wasting the user's time.

It can be understood that the waterproof layer 35 applied to the light source 50 and used to install the light source 50 to achieve waterproof effect, as well as the transparent sealing element 34 with a hydrophobic characteristic set on the lens end surface 43, can also be applied to the embodiments shown in FIGS. 1 to 24.

Figures 29, 30:
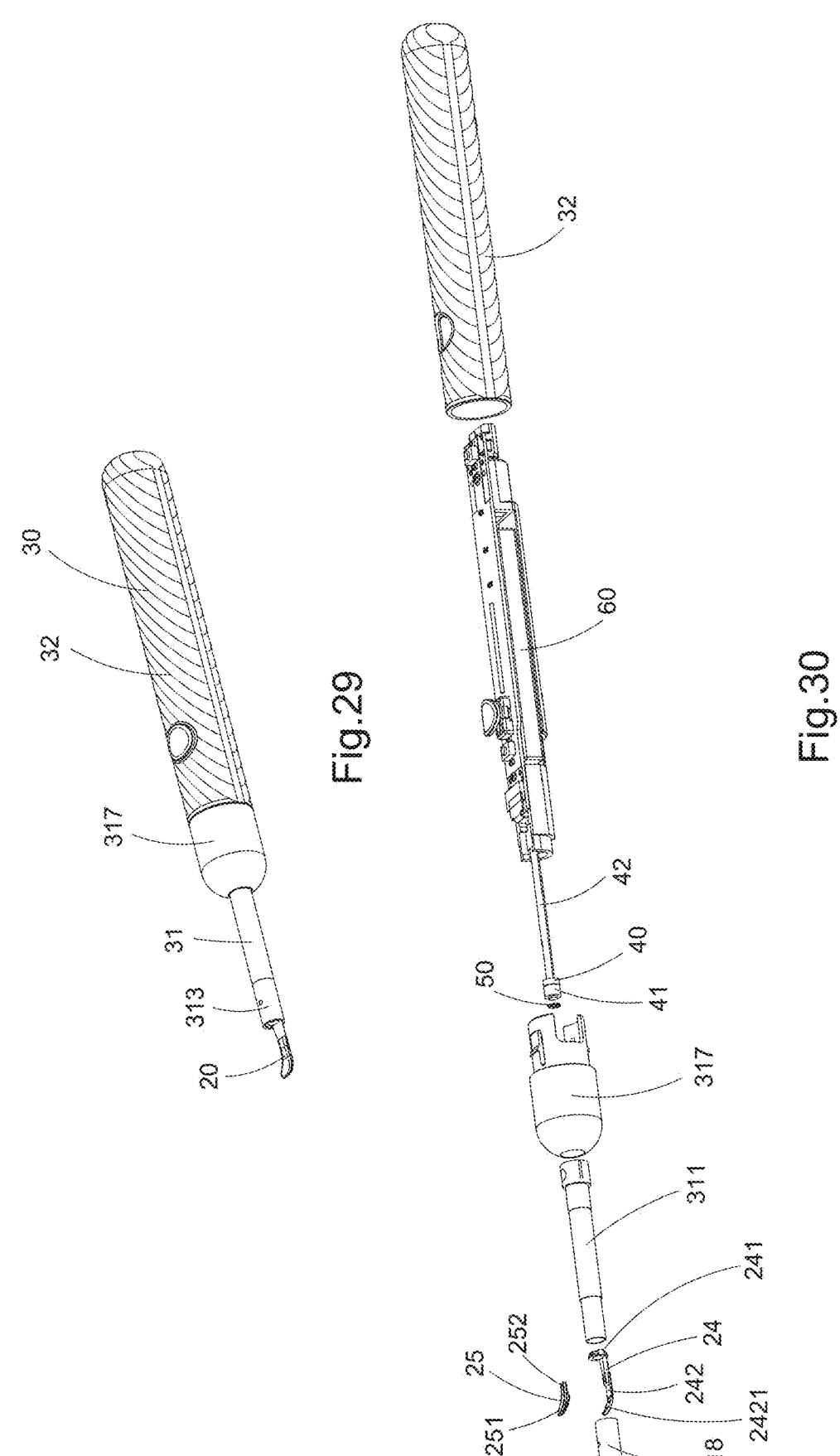
FIG. 29 is a perspective view of the ear cleaning arrangement according to a fifth alternative mode of the second preferred embodiment of the present invention.
FIG. 30 is an exploded view of the ear cleaning arrangement according to the fifth alternative mode of the second preferred embodiment of the present invention.
Figure 31:
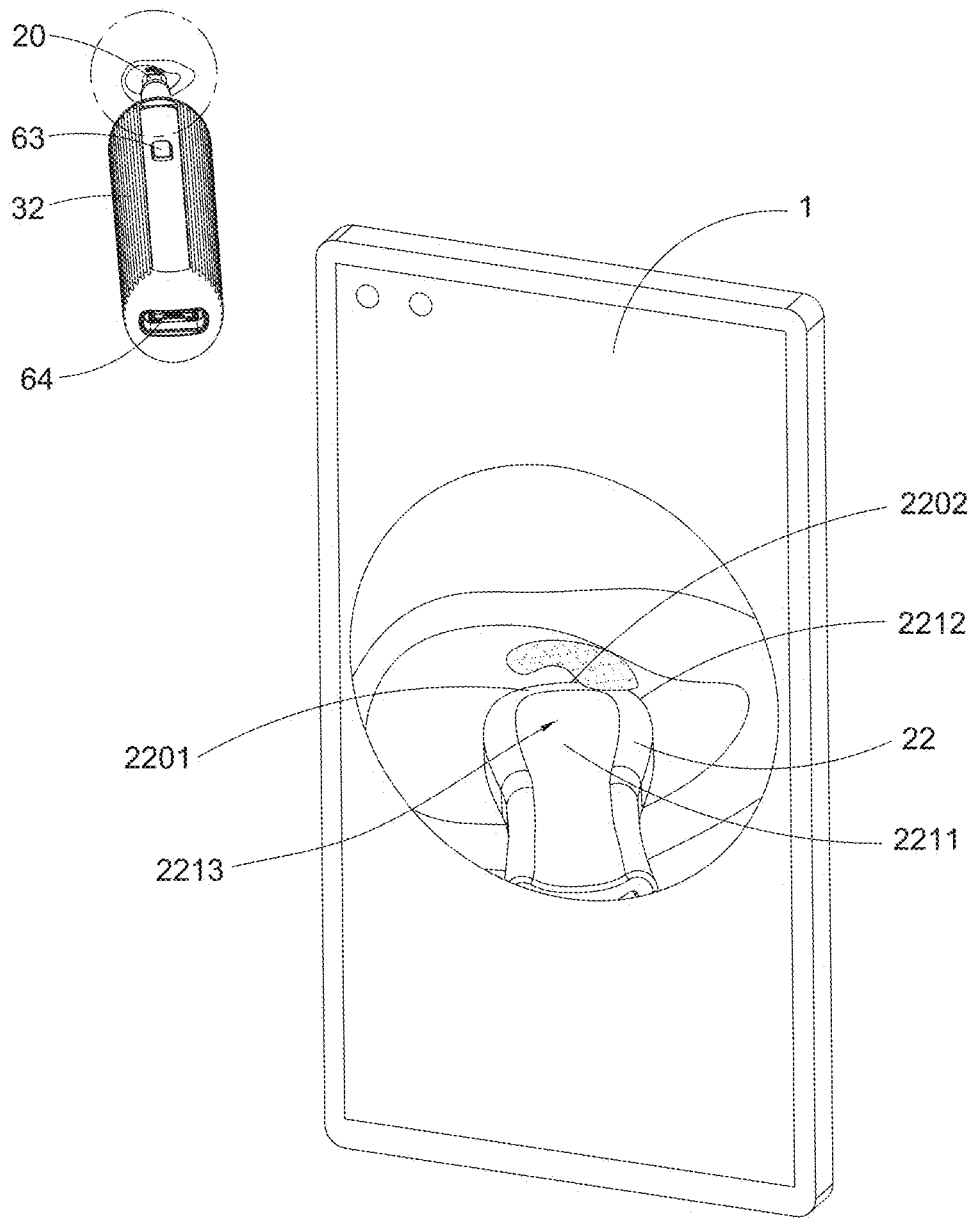
FIG. 31 is a schematic view illustrating the application scenario of the ear cleaning arrangement being wirelessly communicated with an electronic device for earwax cleaning according to the above second preferred embodiment of the present invention.

In this embodiment, the fixing assembly 30 of the fixing rod 31 also comprises a connection part 317, which is integrally extended from the rod body 311 to be assembled with the handle 32. As shown in FIG. 29 to FIG. 30, the fixing assembly 30 of the fixing rod 31 also comprises a connection part 317, which is assembled with the rod body 311 to be assembled with the handle 32. The rod body 311 passes through the connection part 317 to be assembled with the ear spoon assembly 20. As shown in FIG. 31, the ear cleaning arrangement 100 can be wirelessly connected to the electronic device 1 by downloading a mobile application on the electronic device 1 to control the ear device 100. The user can hold the handle 32 to guide the end 2201 of the ear spoon assembly 20 into the ear, and the light emitted by the light source 50 projects into the ear, and the camera 40 captures the image in the ear and the flexible outer spoon 22 of the ear spoon assembly 20, and displays the image information captured by the camera 40 through the electronic device 1 such as a mobile phone or a tablet. The end 2201 of the flexible outer spoon 22 of the ear spoon assembly 20 is located at the center of the circular image field of view, making it convenient to scrape the earwax in the ear into the groove 2213 of the flexible spoon body part 221 and clean it out of the ear along with the ear spoon assembly 20.

It should be noted that in the apparatus and method of this application, the components or steps in different embodiments can be decomposed and/or recombined without departing from the principles of the present invention. These decompositions and/or recombinations should be considered as being included in the inventive concept of this application.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and are subject to change without departure from such principles. Therefore, this invention comprises all modifications encompassed within the spirit and scope of the following claims.

What is claimed is:

1. An ear cleaning arrangement, comprising:

a fixing assembly comprising a handle and a fixing rod extended from the handle, wherein the fixing rod comprises a rod body and a light guide barrel integrally extended from a free end portion of the rod body to form a light guide channel within the light guide barrel, wherein an inner diameter of the rod body is larger than an inner diameter of the light guide barrel to define a step surface therebetween;

a camera supported in the rod body, wherein the camera comprises a camera body having a lens end surface located adjacent to the light guide barrel and defining a center axis at a center of the lens end surface;

a light source which comprises a plurality of light emitting elements radially positioned away from the camera body for emitting light toward the light guide barrel;

a holder, having a receiving cavity and a rear end wall, supported within the rod body behind the light guide barrel, wherein the light emitting elements of the light source are coaxially supported within a front end of the holder while the camera is rearwardly extended from the front end of the holder within the receiving cavity, wherein an outer annular surface of the holder is attached to an inner surface of the light guide barrel; and an ear spoon element which comprises an annular installation part detachably coupled at the free end portion of the rod body, and a spoon body component integrally extended from the annular installation part to form the ear spoon element as a single structure;

wherein an inner diameter of the annular installation part is larger than an outer diameter of the light guide barrel for allowing the light emitted from the light source passing to the spoon body component through the annular installation part;

wherein the holder is made of thermally conductive material for heat dissipation so as to prevent the heat transferring to the ear spoon element;

wherein the fixing assembly further comprises a transparent cover is located on a front side of the camera and the light source, wherein the transparent cover is attached to and sealed between the front end of the holder and the step surface of the light guide barrel, such that the light source and the camera body are sealed in the holder between the transparent cover and the rear end wall of the holder;

wherein the ear spoon element is made of transparent plastic material to allow the light emitted from the light source passing through the ear spoon element;

wherein the ear spoon element has a tip end extended to and located at the center axis of the lens end surface, wherein a center of the tip end of the ear spoon element is extended to and aligned with the center axis of the lens end surface of the camera so as to ensure an image of the tip end of the ear spoon element being captured by the camera.

2. The ear cleaning arrangement according to claim 1, further comprising a waterproof sealant formed at an outer peripheral edge of the transparent cover to seal the transparent cover at the step surface of the light guide barrel, wherein an inner diameter of the holder is equal to the inner diameter of the light guide barrel, wherein the inner diameter of the annular installation part is larger than the inner diameter of the holder.

3. The ear cleaning arrangement according to claim 2, wherein two of the light emitting elements serve as two middle light emitting elements located along a diameter line of the lens end surface, wherein center positions of the two middle light emitting elements, the center of the lens end surface of the camera, and the center position of the tip end of the ear spoon element are located in a same plane, wherein the center of the tip end of the ear spoon element is located between the two middle light emitting elements, such that the center of the tip end of the ear spoon element and the two middle light emitting elements are located along the diameter line of the lens end surface at a position that the center of the tip end of the ear spoon element is located between the two middle light emitting elements from a front view of the fixing assembly, so as to ensure the center of the tip end of the ear spoon element at a center of a field of view of the camera.

4. The ear cleaning arrangement according to claim 1, wherein the ear spoon element, which is made of a mold-injected element consisting of two materials, comprises an inner layer of polycarbonate and an outer layer of thermoplastic polyurethane elastomer.

5. The ear cleaning arrangement according to claim 1, wherein a thermal conductivity of the ear spoon element is lower than that of the fixing rod and is lower than that of the holder, thereby preventing heat from being transferred from the fixing rod to the spoon body component of the ear spoon element.

6. The ear cleaning arrangement according to claim 1, wherein an outer diameter of the annular installation part is the same as an outer diameter of the rod body, so that when the annular installation part is assembled on the outer surface of the light guide barrel, an outer surface of the annular installation part and an outer surface of the rod body are connected to form an integral cylindrical outer surface.

7. The ear cleaning arrangement according to claim 1, wherein the transparent cover is sealed behind light guide barrel and supported within the annular installation part.

8. The ear cleaning arrangement according to claim 7, wherein the transparent cover is attached to a front side of the lens end surface of the camera at the front end of the holder.

9. The ear cleaning arrangement according to claim 1, wherein the holder is adhered to the step surface of the light guide barrel to retain the holder within the rod body and behind the light guide barrel.

10. The ear cleaning arrangement according to claim 1, wherein the camera further comprises a connection circuit board rearwardly extended from the camera body within the holder and extended out of the holder through a slit of the rear end wall of the holder into the handle.

*     *     *     *     *